US006793926B1

(12) United States Patent
Rasty et al.

(10) Patent No.: US 6,793,926 B1
(45) Date of Patent: Sep. 21, 2004

(54) METHODS FOR PRODUCTION OF A RECOMBINANT ADENO-ASSOCIATED VIRUS

(75) Inventors: Siyamak Rasty, Wilmington, DE (US); Matthew A. Gonda, Vestavia Hills, AL (US); Haifeng Chen, Media, PA (US)

(73) Assignee: Genovo, Inc., Seattle, WA (US)

( * ) Notice: Subject to any disclaimer, the term of this patent is extended or adjusted under 35 U.S.C. 154(b) by 0 days.

(21) Appl. No.: 09/578,561

(22) Filed: May 25, 2000

Related U.S. Application Data

(60) Provisional application No. 60/136,650, filed on May 27, 1999.

(51) Int. Cl.$^7$ ................................................ A61K 39/12
(52) U.S. Cl. .............................. 424/199.1; 424/184.1; 424/204.1; 424/233.1; 435/69.1; 435/235.1; 435/320.1; 435/455; 435/456; 435/457; 514/44; 536/23.1; 536/23.72
(58) Field of Search .......................... 424/184.1, 199.1, 424/204.1, 233.1; 435/69.1, 91.32, 235.1, 320.1, 456, 457, 455; 536/23.1, 23.72; 514/44

(56) References Cited

U.S. PATENT DOCUMENTS

| 5,436,146 A | 7/1995 | Shenk et al. ............. 435/172.3 |
| 5,658,785 A | 8/1997 | Johnson ...................... 435/367 |
| 5,672,510 A | 9/1997 | Eglitis et al. ............... 435/325 |
| 5,731,182 A | 3/1998 | Boyce ......................... 435/183 |
| 5,753,500 A | 5/1998 | Shenk et al. ............. 435/320.1 |
| 5,837,484 A | 11/1998 | Trempe et al. ............. 435/69.1 |
| 5,851,806 A | 12/1998 | Koveski et al. ........... 435/91.41 |
| 5,851,826 A | 12/1998 | Fraefel et al. ............. 435/325 |
| 5,856,152 A | 1/1999 | Wilson et al. ........... 435/172.3 |
| 5,871,986 A | 2/1999 | Boyce ......................... 435/183 |
| 6,338,953 B1 * | 1/2002 | Boyce et al. .............. 435/69.7 |
| 6,387,670 B1 * | 5/2002 | Leblois-Prehaud et al. ............ 424/93.2 |
| 6,475,769 B1 | 11/2002 | Wilson et al. ........... 435/235.1 |
| 2003/0175974 A1 | 9/2003 | Allen |

FOREIGN PATENT DOCUMENTS

| AU | 731106 | 5/1998 |
| AU | 725843 | 10/2000 |
| EP | 0549721 | * 4/1994 |
| FR | 2756297 | 5/1998 |
| WO | WO 95/02697 A1 | 1/1995 |
| WO | WO 96/17947 | 6/1996 |
| WO | WO 98/10088 A1 | 3/1998 |
| WO | WO 98/22607 A1 | 5/1998 |
| WO | WO 98/45462 A1 | 10/1998 |
| WO | WO 99/15685 A1 | 4/1999 |

OTHER PUBLICATIONS

Shoji et al. Efficient gene transfer into various mammlian cells, including non–hepatic cells, by baculoviral vectors. Journal of General Virology (1997)vol. 78, pp. 2657–2664.*

Kockanek et al. A new adenoviral vector: Replacement of all viral coding sequences with 28 kB of DNA independently expressing both full–length dystophin and beta–galactosidase, Proceedings of the National Academy of Sciences (1996) vol. 93, pp. 5731–5736.*

Amaltifano et al. (1996). "Improved Adenovirus Packagin Cell Lines to Support the Growth of Replication–Defective Gene–Delivery Vectors," *Proc. Natl. Acad. Sci. USA* 93:3352–3356.

Andersen et al. (1993). "Herpesvirus–Mediated Gene Delivery into the Rat Brain: Specificity and Efficiency of the Neuron–Specific Enolase Promoter," *Cell. Mol. Neurobiol.* 13(5):503–515.

Arbuthnot et al. (1996). "In Vitro and In Vivo Hepatoma Cell–Specific Expression of a Gene Transferred with an Adenoviral Vector," *Hum. Gene Ther.* 7:1503–1514.

Barsoum et al. (1997). "Efficient Transduction of Mammalian Cells by a Recombinant Baculovirus Having the Vesicular Stomatitis Virus G Glycoprotein," *Human Gene Therapy* 8:2011–2018.

Bilboa et al. (1997). "Adenoviral/Retroviral Vector Chimeras: A Novel Strategy to Achieve High Efficiency Stabel Transduction In Vivo," *Faseb J.* 11:624–634.

Boshart et al. (1985). "A Very Strong Enhancer is Located Upstream of an Immediate Early Gene of Human Cytomegalovirus," *Cell* 41:521–530.

Boyce et al. (1996). "Baculovirus–Mediated Gene Transfer into Mammalian Cells," *Proc. Natl. Acad. Sci. USA* 93:2348–2352.

Carbonell et al. (1987). "Baculovirus Interaction with Non-target Organisms: A Virus–Borne Reporter Gene is Not Expressed in Two Mammalian Cell Lines," *Appl. Environ. Microbiol.* 53(7):1412–1417.

(List continued on next page.)

Primary Examiner—Ulrike Winkler
(74) Attorney, Agent, or Firm—Morrison & Foerster LLP

(57) ABSTRACT

This invention relates to novel nonmammalian carrier vectors and viruses useful in the production of high titers of recombinant viruses which may contain foreign DNA inserts or which may be point-mutated or deleted viruses, and methods of producing those viruses. The nonmammalian carrier vector ("carrier vector") is a chimeric vector which includes those portions of a nonmammalian virus backbone which allow replication in a nonmammalian host cell. The carrier vector includes various nucleic acid cassettes, which may include an embedded recombinant viral genome containing a desired transgene, components necessary for production of a replication-defective recombinant virus containing the transgene, and domains that permit the carrier vector to bind to mammalian cells. The invention also provides methods of producing high concentrations of recombinant virus as a substantially homogeneous preparation, compositions to produce the recombinant virus, and novel recombinant viruses.

21 Claims, 10 Drawing Sheets

OTHER PUBLICATIONS

Carter, B. J. (1990). "The Growth Cycle of Adeno–Associated Virus," Chapter 10 In Handbook of Parvoviruses. P. Tijsser ed., CRC Press, pp. 155–168.

Chen, H. and R. Padmanabhan. (1994). "A Modified Method for Isolation of Recombinant Vaccinia Virus," Biotechniques 17(1):41–42.

Chen et al. (1996). "Expression of Rat Bone Sialoprotein Promoter in Transgenic Mice," J. Bone Miner. Res. 11(5):654–664.

Coffin J.M. (1990). "Molecular Mechanisms of Nucleic Acid Intergration," J. Med. Virol. 31(1):43–49.

Cone et al. (1984). "High–Efficiency Gene Transfer into Mammalian Cells: Generation of Helper–Free Recombinant Retrovirus with Broad Mammalian Host Range," Proc. Natl. Acad. Sci. USA 81:6349–6353.

Eidelman et al. (1996). "pH–Dependent Fusion Induced by Vesicular Stomatitis Virus Glycoprotein Reconstituted into Phospholipid Vesicles," J. Biol. Chem. 259(7):4622–4628.

Fisher et al. (1996). "Transduction With Recombinant Adeno–Associated Virus for Gene Therapy is Limited by Leading–Strand Synthesis," J. Virol. 70(1):520–532.

Gao et al. (1998). "High–Titer Adeno–Associated Viral Vectors from a Rep/Cap Cell Line and Hybrid Shuttle Virus," Hum. Gene. Ther. 9(16):2353–2362.

GenBank Accession No. L22852. (Mar. 29, 2001). "Autographa californica nucleopolyhedrovirus clone C6, complete genome." located at http://www.ncbi.nlm.nih.gov/entrez/query.fcgi?CMD=search&DB=nucleotide on Jan. 18, 2002, 74 pages.

Gossen M. and H. Bujard. (1992). "Tight Control of Gene Expression in Mammalian Cells by Tetracycline–Responsive Promoters," Proc. Natl. Acad. Sci. USA 89:5547–5551.

Gossen et al. (1995). "Transcriptional Activation by Tetracyclines in Mammalian Cells," Science 268:1766–1769.

Hansal et al. (1998). "Cutting Edge: Induction of Antigen–Specific Hyporesponsiveness by Transplantation of Hemopoietic Cells Containing an MHC Class I Transgene Regulated by a Lymphocyte–Specific Promoter," J. Immunol. 161:1063–1068.

Harvey D.M. and C.T. Caskey. (1998) "Inducible Control of Gene Expression: Prospects for Gene Therapy," Curr. Opin. Chem. Biol. 2:512–518.

Hoffman et al. (1995). "Efficient Gene Transfer Into Human Hepatocytes by Baculovirus Vectors," Proc. Natl. Acad. Sci. U.S.A. 92:10099–10103.

Horwich et al. (1990). "Synthesis of Hepadnavirus Particles that Contain Replication–Defective Duck Hepatitis B Virus Genomes in Cultured HuH7 Cells," J. Virol. 64(2):642–650.

Jones, N. and T. Shenk. (1978). "Isolation of Deletion and Substitution Mutants of Adenovirus Type 5," Cell 13(1):181–188.

Li et al. (1999). "Synthetic Muscle Promoters: Activities Exceeding Naturally Occuring Regulatory Sequences," Nat. Biotech. 17:241–245.

Macejak D.G. and P. Sarnow. (1991). "Internet Initiation of Translation Mediated by the 5' Leader of a Cellular mRNA," Nature 353(6339):90–94.

Magari et al. (1997) "Pharmacologic Control of a Humanized Gene Therapy System Implanted into Nude Mice," J. Clin. Invest. 100:2865–2872.

Miller et al. (1985). "Generation of Helper–Free Amphotropic Retroviruses That Transduce a Dominant–Acting, Methotrexate–Resistant Dihydrofolate Reductase Gene," Mol. Cell. Biol. 5(3):431–437.

Miller et al. (1986). "Redesign of Retrovirus Packaging Cell Lines to Avoid Recombination Leading to Helper Virus Production," Mol. Cell. Biol. 6(8):2895–2902.

Miyatake et al. (1997). "Transcriptional Targeting of Herpes Simplex Virus for Cell–Specific Replication," J. Virol. 71(7):5124–5132.

No et al. (1996), "Ecdysone–Inducible Gene Expression in Mammalian Cells and Transgenic Mice," Proc. Natl. Acad. Sci. USA 93:3346–3351.

Palombo et al. (1998). "Site–Specific Integration in Mammalian Cells Mediated by a New Hybrid Baculovirus–Adeno–Associated Virus Vector," J. Virol. 72(6):5025–5034.

Pelletier J. and N. Sonenberg (1988). "Internal Initiation of Translation of Eukaryotic mRNA Directed by a Sequence Derived from Poliovirus RNA," Nature 334(6180):320–325.

Piccioli et al. (1991). "Neuroantibodies: Molecular Cloning of a Monoclonal Antibody Against Substance P for Expression in the Central Nervous System," Proc. Natl. Acad. Sci. USA 88:5611–5615.

Piccioli et al. (1995). "Neuroantibodies: Ectopic Expression of a Recombinant Anti–Substance P Antibody in the Central Nervous System of Transgenic Mice," Neuron 15:373–384.

Rivera et al. (1996). "A Humanized System for Pharmacologic Control of Gene Expression," Nat. Medicine 2(9):1028–1032.

Sambrook et al. (1989). Molecular Cloning–A Laboratory Manual. Cold Spring Harbor Laboratory Press, pp. 3.18 & 3.26.

Sandig et al. (1996). "HBV–Derived Promoters Direct Liver–Specific Expression of an Adenovirally Transduced LDL Receptor Gene," Gene Ther. 3:1002–1009.

Sorge et al. (1984). "Amphotropic Retrovirus Vector System for Human Cell Gene Transfer," Mol. Cell. Biol. 4(9):1730–1737.

Speiss M. (1990). "The Asialoglycoprotein Receptor: A Model for Endocytic Transport Receptors," Biochem. 29(43):10009–10018.

Stein et al. (1997). "The Osteocalcin Gene: A Model for Multiple Parameters of Skeletal–Specific Transcriptional Control," Mol. Biol. Rep. 24:185–196.

Volkman L.E. and P.A. Goldsmith (1983). "In Vitro Survey of Autographa californica Nuclear Polyhedrosis Virus Interaction with Nontarget Vertebrate Host Cells," Appl. Environ. Microbiol. 45(3):1085–1093.

Wang et al. (1997a) "Ligand–Inducible and Liver–Specific Target Gene Expression in Transgenic Mice," Nat. Biotech. 15:239–243.

Wang et al. (1997b). "Positive and Negative Regulation of Gene Expression in Eukaryotic Cells with an Inducible Tanscriptional Regulator," Gene Ther. 4:432–441.

Xiao et al. (1998). "Production of High–Titer Recombinant Adeno–Associated Virus Vectors in the Absence of Helper Adenovirus," J. Virol. 72(3):2224–2232.

\* cited by examiner

FIGURE 2
A.
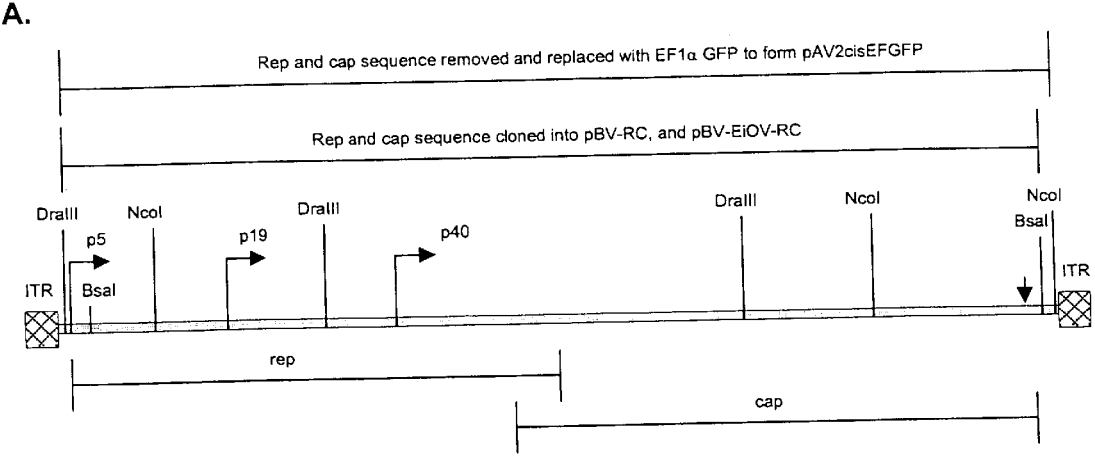
B.
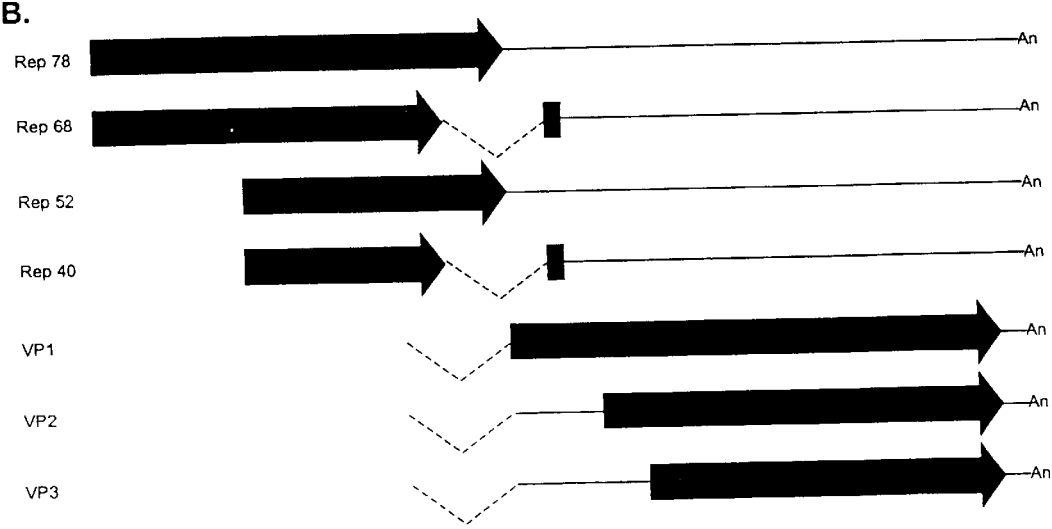

pAdDeltaF6-RC
19780 bp pBV-EiOV-cisEFGFP-E1
21510 bp pAc-cisEFGFP
9492 bp pBV-EiOV-RC-EBVOri
19522 bp pBVcisEFGFP-EBVOri
15149 bp

FIGURE 6

Transduce with recombinant
baculovirus for 72 hours

BV-EiOV-RC

293-CG3 → rAAV

Collect cell lysates rAAV stock

METHODS FOR PRODUCTION OF A RECOMBINANT ADENO-ASSOCIATED VIRUS

CROSS REFERENCE TO RELATED APPLICATION

This application claims the benefit of priority to U.S. provisional patent application serial No. 60/136,650 filed May 27, 1999.

TECHNICAL FIELD OF THE INVENTION

This invention relates to novel nonmammalian carrier vectors and viruses useful in the production of high titers of recombinant viruses which may contain foreign DNA inserts or which may be point-mutated or deleted viruses, and methods of producing those viruses. The nonmammalian carrier vector ("carrier vector") is a chimeric vector which includes those portions of a nonmammalian virus backbone which allow replication in a nonmammalian host cell. The carrier vector includes various nucleic acid cassettes, which may include an embedded recombinant viral genome containing a desired transgene, components necessary for production of a replication-defective recombinant virus containing the transgene, and domains that permit the carrier vector to bind to mammalian cells. The invention also provides methods of producing high concentrations of recombinant virus as a substantially homogeneous preparation, compositions to produce the recombinant virus, and novel recombinant viruses.

BACKGROUND OF THE INVENTION

A recombinant virus carrying a foreign DNA insert may be used to deliver genes to cells, where the gene may be expressed, if desired, to permit production of recombinant proteins in vitro or in vivo, vaccination of human and non-human mammals, or treatment or amelioration of diseases or genetic defects in humans or non-human mammals. One may treat or ameliorate diseases or genetic defects by providing normal gene products, increased levels of gene products or by blocking endogenous production of a gene, whose expression would be deleterious to the cell or organism.

Methods for delivering an exogenous gene to a mammalian cell include the use of mammalian viral vectors, such as those which are derived from retroviruses, adenoviruses, herpes viruses, vaccinia viruses, polio viruses, adeno-associated viruses, hybrid viruses (e.g., hybrid adenovirus-AAV, see U.S. Pat. No. 5,856,152) and the like. Other methods include direct injection of DNA, biolistic administration of DNA, electroporation, calcium phosphate precipitation, as well as methods of administration which utilize ligand-DNA conjugates, liposome conjugates of DNA, polycation-DNA complexes or adenovirus-ligand-DNA conjugates.

A transgene is a nucleic acid encoding a protein of interest; it may be a gene to allow for genetic or drug selection, e.g., a gene conferring resistance to antibiotics, or a reporter gene allowing detection, e.g., by color in the case of the use of green fluorescent protein. Alternatively, the transgene may be one that is useful for corrective applications. For instance, a transgene may be a normal gene that replaces or augments the function of a patient's defective gene. The transgene may be one that counteracts the effects of a disease, such as introduction and expression of a gene that is distinct from the one that it replaces or augments, but which has the same function or compensates for the defective gene's function. The transgene may be a gene which blocks or represses the expression of a malfunctioning, mutated, or viral gene in the patient, thereby giving rise to a corrective effect. A transgene may also be used for immunization against various agents, by provoking an immunogenic response in an animal. Delivery of therapeutic transgenes to a patient thus effects a correction of a defect or prevention of disease. The transgene also may be one which is useful for production of proteins in vitro, such as for large-scale production of therapeutic proteins.

Appropriate genes for expression in the cell include, without limitation, those genes which are normally expressed in cells but whose products are produced in insufficient amounts. Alternatively, the appropriate gene for expression is one which expresses a normal gene product which replaces a defective gene product, encodes ribozymes or antisense molecules which repair or destroy mutant cellular RNAs expressed from mutated genes, or modifies or destroys viral RNAs. Transgenes used for production of proteins in vitro include proteins such as secreted factors, including hormones, growth factors and enzymes.

Many gene therapy methods involve supplying an exogenous gene to overcome a deficiency in the expression of a gene in a patient. Some of these deficiencies are congenital and are due to a mutation in a particular gene in all the cells of the patient. For instance, in cystic fibrosis, there are one or more mutations in the gene encoding the cystic fibrosis transmembrane conductance regulator (CFTR) which prevents the CFTR protein from functioning properly. In other cases, a deficiency in gene expression is due to an accident or disease that occurs during the patient's life. For instance, in Type I diabetes mellitus, the β pancreatic islet cells, which produce insulin, are destroyed, such that patients with this disease can no longer synthesize insulin. In other cases, the endogenous gene may be structurally normal but is not produced in high enough quantities due to disease, medical treatment or other environmental conditions, or mutations in the regulatory elements of the endogenous gene. For example, there are a number of blood disorders, such as anemia, in which there is insufficient production of red blood cells, which may be treated with erythropoietin (EPO) or with a transgene encoding EPO. Transgenes may also be used for genetic immunization, i.e., to elicit an immune response to a pathogen in an animal, including humans. For instance, a transgene may include a sequence from a viral, bacterial or fungal pathogen, such as influenza virus, human immunodeficiency virus (HIV), or mycobacterium tuberculosis.

Certain methods are amenable to targeted delivery of the exogenous gene to specific tissues, such as liver tissue. One method of delivering genes to specific cells relies upon the function of a cell-specific receptor. The asialoglycoprotein receptor (ASGP-R), which is present on the surface of hepatocytes (Spiess et al., 1990, Biochem. 29:10009–10018), is a lectin which has affinity for the terminal galactose residues of glycoproteins, and has been used to target gene delivery to liver hepatocytes. For example, a DNA complex is bound to a ASGP-R on the cell surface, allowing subsequent endoyctosis by the liver hepatocyte.

Viruses that are commonly used in gene delivery applications are modified by replacing viral nucleic acid with a desired transgene. Frequently, DNA removed from the virus encodes proteins necessary for viral replication or encapsidation, in which case the recombinant virus containing a transgene is replication-deficient and will not replicate or encapsidate in the host. To permit replication and encapsidation, current methods recognize that those portions of DNA which have been deleted must be supplied by wild-type or modified viruses or by plasmids containing DNA encoding the required gene products. Supplying wild-type or modified virus may result in recombinant virus stocks contaminated with wild-type or modified virus. Supplying plasmids encoding the required gene products through cotransfection results in low efficiency of recombinant virus production, as well as recombination events which yield wild-type virus contaminants.

A number of different viruses have been used to deliver a transgene to mammalian cells. These viruses include retrovirus, hepatitis B virus (HBV), adenovirus, adeno-associated virus (AAV) and herpesvirus. AAV possesses unique features that make it attractive as a vector for delivering foreign DNA (i.e., a transgene) to cells, and various groups have studied the potential use of AAV in the treatment of disease states.

AAV is a parvovirus, the genome of which is about 4.7 kb in length, including 145 nucleotide inverted terminal repeats (ITRs). The AAV genome encodes two genes, rep and cap, each of which expresses a family of related proteins from separate open reading frames and produced as a result of alternative mRNA splicing. Rep polypeptides (rep78, rep68, rep52, and rep40) are involved in replication, rescue and integration of the AAV genome. Cap proteins (VP1, VP2, and VP3) form the virion capsid. Flanking the rep and cap open reading frames at the 5' and 3' ends of the AAV genome are the 145 bp ITRs, the first 125 bp of which are capable of forming Y- or T-shaped duplex structures. The entire nucleic acid encoding rep and cap can be excised and replaced with a transgene [B. J. Carter, in "Handbook of Parvoviruses", ed., P. Tijsser, CRC Press, pp. 155–168 (1990)]. The ITRs represent the minimal sequence required for replication, rescue, packaging, and integration of the AAV genome.

When this nonpathogenic human virus infects a human cell, the viral genome integrates into chromosome 19 resulting in latent infection of the cell. Production of infectious virus and replication of the virus does not occur unless the cell is coinfected with a lytic helper virus, such as adenovirus (Ad) or herpesvirus. Upon infection with a helper virus, the AAV provirus is rescued and amplified, and both AAV and helper virus are produced. The infecting parental ssDNA is converted to duplex replicating form (RF) DNAs in a rep dependent manner. The rescued AAV genomes are packaged into preformed protein capsids (icosahedral symmetry approximately 20 nm in diameter) and released as infectious virions that have packaged either+or−ss DNA genomes following cell lysis. However, progress towards establishing AAV as a transducing vector for the delivery of DNA in the form of a desired transgene has been slow for a variety of reasons.

Replacing the rep and cap sequences with a desired transgene yields a recombinant virus capable of delivering the transgene to target host cells. However, because AAV requires a particular genome packaging size, addition of a transgene results in deletion of necessary gene functions for rep and cap. In current methods, necessary gene functions replaced by the transgene are supplied by viruses or additional plasmids. Furthermore, the requirement by AAV for helper virus functions also requires the use of helper viruses (either wildtype or crippled viruses) or plasmids containing the helper virus functions.

One method that has been used to produce recombinant AAV (rAAV) vectors comprises co-transfecting eukaryotic cells with a plasmid containing rAAV (the cis plasmid) and a plasmid containing rep and cap (the trans plasmid), and infecting the cells with a helper virus (e.g., adenovirus or herpes virus). See U.S. Pat. No. 5,753,500. The disadvantage of this method is that the rAAV vector stock is contaminated with helper virus, which is labor-intensive and difficult to separate from the helper virus, and co-transfection of two plasmids along with infection by a helper virus is inefficient and cannot be easily scaled up for industrial production of rAAV.

A second method that has been used to produced rAAV involves a triple plasmid transfection of eukaryotic cells. In this method, one plasmid carries the transgene and ITRs (the cis plasmid), a second plasmid encodes the rep and cap genes (the trans plasmid), and the third plasmid encodes the helper virus functions, i.e. adenoviral genes such as E1a, E1b, E2a and E4 (the helper plasmid). The disadvantage of this method is that a triple transfection is also inefficient and is difficult to scale up.

A third method involves the use of a packaging cell line such as one including AAV functions rep and cap. See U.S. Pat. No. 5,658,785 and U.S. Ser. No. PCT US98/19463. The packaging cell line may be transfected with a cis plasmid comprising the transgene and ITRs, and infected by wild-type adenovirus (Ad) helper. See U.S. Pat. No. 5,658,785. Alternatively, the packaging cell line may be co-infected by a hybrid Ad/AAV, in which a hybrid Ad vector caries the cis plasmid in the E1 locus (see U.S. Pat. No. 5,856,152), and by a wild-type or mutant Ad that supplies E1. The disadvantage of this method is that wild-type Ad may be produced, which must be separated from the rAAV vector before use in a patient.

Thus, current methods of producing recombinant AAV are incapable of yielding the high amounts of essentially homogeneous virus for pharmaceutical compositions needed for the treatment of a large number of patients in a easily scaled industrial production.

Nonmammalian viruses have been used to transiently express particular individual exogenous proteins in either mammalian or non-mammalian cells. For example, viruses of the family Baculoviridae, or "baculoviruses", which normally infect members of the order Lepidoptera, have been used to express exogenous genes in insect cells. Baculoviruses have also been reported to enter mammalian cells, and baculoviral DNA has been detected in nuclear extracts of mammalian cells (Volkman et al., 1983, Appl. Environ. Microbiol. 45:1085–1093). While one report of baculovirus-mediated gene expression in mammalian cells has appeared, the authors later attributed the apparent reporter gene activity to the reporter gene product being carried into the cell after a prolonged incubation of the cell with the virus (Carbonell et al., 1987, Appl. Environ. Microbiol. 53:1412–1417). These authors reported that, when the exogenous gene gains access to the cell as part of the baculovirus genome, the exogenous gene is not expressed de novo. Subsequent studies have demonstrated baculovirus-mediated gene expression of particular proteins in mammalian cells (Boyce et al., 1996, Proc. Natl. Acad. Sci. USA, 93:2348–2352).

While baculovirus has been used for expressing particular proteins in a mammalian cell, see U.S. Pat. No. 5,731,182, baculovirus has not been used to produce pharmaceutical compositions of replication-deficient recombinant virus using an easily scaled industrial process. As disclosed in U.S. Pat. No. 5,731,182, the genome of the baculovirus may be modified by insertion of ligand DNA, which comprises a gene encoding a mammalian receptor specific protein that allows the baculovirus to bind and enter mammalian cells. The nonmammalian virus infecting the mammalian cells allows only for transient expression of the transgene within the mammalian cell. In addition, the methods disclosed in U.S. Pat. No. 5,731,182 do not result in production of an altogether distinct, essentially homogeneous recombinant virus, at high titers.

The problem of generating recombinant replication-deficient virus that is produced in the absence of helper viruses and by an efficient method that is applicable to large-scale industrial production has not been solved until the present invention. Current viral production methods include costly and time consuming purification and concentration steps, and are incapable of producing sufficient recombinant virus for pharmaceutic applications. In the case of AAV, for example, current methods produce at most on the order of $10^4$–$10^5$ genomic copies (gc) of recombinant virus per producer cell. Similarly, current methods are suitable for producing recombinant adenovirus in amounts on the order of $10^4$ particles per producer cell, and retroviruses in amounts on the order of $10^2$–$10^4$ colony forming units (cfu) per producer cell. Current production methods result in contaminating helper virus which must be inactivated and/or removed from the final products prior to pharmaceutical application. Thus, there exists an unfulfilled need for a method of manufacturing recombinant mammalian virus at high titers free of other contaminating virus in order to produce recombinant viruses capable of delivering a desired transgene to mammalian cells, or immunizing cells against viral or bacterial infection by the use of such recombinant viruses, in a stable fashion.

SUMMARY OF THE INVENTION

The invention exploits the properties of nonmammalian and mammalian viruses to create novel chimeric vectors and viruses for the manufacture of an essentially homogeneous recombinant virus preparation in the absence of contaminating helper virus using a process that may be easily scaled for industrial production. The essentially homogeneous recombinant virus may be used for various purposes, including delivering a desired transgene to mammalian cells for pharmaceutic applications including immunization and correction of genetic defects; transient and stable gene transfer in vivo, in vitro and ex vivo; production of proteins in vivo or in vitro; and other methods in which high levels of gene transduction into a cell are required, e.g., in the production of expression libraries for screening compounds or for introducing genes into cells that are not easily transfected.

The carrier vector of the invention is a chimeric vector backbone derived from the nucleic acid of a nonmammalian virus, and includes one or more of the following elements: 1) an embedded recombinant viral genome; 2) nucleic acid sequences which encode proteins required for replication and encapsidation of the recombinant virus genome; 3) nucleic acid sequences encoding helper functions (if the recombinant virus to be produced is helper-dependent, e.g., AAV); 4) nucleic acid sequences encoding a ligand that can interact with a mammalian cell; and 5) regulatory control sequences that regulate nucleic acid sequences in the nonmammalian virus backbone or in a replication-deficient portion or modification thereof The carrier vector may also include any other nucleic acid sequences that are required to produce a replication-deficient recombinant virus.

In one embodiment of the invention, one or more carrier vectors may comprise all of the elements required to produce a replication-deficient recombinant vector in a particular host cell or cell line. The number and type of elements that are required will depend upon the particular host cell used and the type of recombinant vector produced. For instance, if a recombinant AAV vector is desired and the host cell line is one which has rep and cap stably integrated in its genome, the carrier vector or vectors would comprise 1) an embedded recombinant viral genome comprising the AAV ITRs and the transgene and 2) separate helper functions, which may include any nucleic acid sequence required for replication and encapsidation of the rAAV. For instance, these helper functions may include any one or a combination of E1, E2a, E4ORF6 and VAI from adenovirus (Ad). If a recombinant AAV vector is to be produced in a host cell line that does not express rep and cap, then the carrier vector or vectors may also include the DNA sequences encoding rep and cap.

Alternatively, if a recombinant retrovirus is desired, the carrier vector or vectors would comprise 1) an embedded recombinant viral genome comprising the retroviral LTRs and the transgene of interest driven from the retroviral LTRs or from a heterologous promoter, and 2) DNA sequences encoding any one or a combination of gag, pol and env for the functions of replication and encapsidation of the retrovirus not supplied in the host cell. In a preferred embodiment, all of the required elements to produce a recombinant virus in a particular host cell are contained on a single carrier vector because the use of a single carrier vector having all functions not supplied by a host cell increases the efficiency of transduction, and can be more easily scaled for industrial production of the embedded recombinant virus.

In an alternative embodiment, the carrier vector comprises an embedded recombinant viral genome, and any required replication, encapsidation and/or helper functions are provided by a helper virus or a plasmid.

The embedded recombinant viral genome may comprise a transgene and DNA elements required for replication of a mammalian virus. The transgene comprises the gene of interest, regulatory elements to regulate its expression, and an optional DNA spacer. The transgene is flanked by the DNA elements required for replication of a mammalian virus, such as the ITRs of AAV, the LTRs of retrovirus, or the ITRs of adenovirus. The recombinant viral genome is embedded within the nonmammalian virus backbone, optionally along with one or more of the other DNA sequences listed above, resulting in a chimeric carrier vector of the present invention.

In an alternative embodiment, the embedded recombinant viral genome does not contain a transgene but the recombinant viral genome itself contains point mutations or deletions. In this embodiment, the point mutations or deletions function to attenuate the replication of the subsequently-produced recombinant virus. The attenuated recombinant virus may be any virus which could be useful for vaccination, including, without limitation, picornaviruses such as poliovirus; hepatitis viruses such as hepatitis B and hepatitis C; cold-adapted respiratory syncytial virus (RSV); cold-adapted influenza virus; parainfluenza virus types 1, 2 and 3; and rotavirus.

The carrier vector is replication-proficient in its native host cells. For example, employing a baculovirus backbone results in a chimeric carrier vector that is replication-proficient in insect cells. In contrast, the embedded recombinant viral genome, optionally containing a transgene, is unable to excise, replicate, and package into virions because its promoters are inactive in insect cells. However, once the chimeric carrier vector infects a mammalian cell, the essential gene products required for replication and packaging of the carrier vector in its permissive native cell are no longer expressed. Thus, the carrier vector does not replicate in mammalian cells, and instead exists transiently within the mammalian cell.

In contrast, once the carrier vector has infected a mammalian cell, the mammalian regulatory sequences within the carrier vector controlling the embedded recombinant viral genome and other mammalian DNA sequences are activated, such that the recombinant viral genome is capable of being excised from the carrier vector and replicated. The capsid proteins which form the capsid of the recombinant virus are expressed such that the recombinant viral genome is encapsidated, which yields an infectious recombinant virus. The recombinant virus is essentially free of carrier vector because the carrier vector is not replicated in mammalian cells.

In a preferred embodiment, the recombinant virus is replication-deficient because there are no replication or helper functions present in the newly formed virions; i.e., the recombinant virus lacks part or all of the coding regions of the native virus genome. In embodiments of the invention in which the recombinant virus is helper-dependent, such as rAAV, the recombinant virus lacks both functional replication and encapsidation functions. In embodiments of the invention in which the recombinant virus is not helper-dependent, the recombinant virus lacks functional replication coding regions or other essential genes.

In cases where helper functions are required for recombinant virus production, recombinant virus may be produced without the need for coinfection and subsequent production of helper virus if a carrier vector includes the necessary helper functions. Thus, the invention yields lysates of substantially pure and essentially homogeneous preparations of the particular recombinant virus of interest in the absence of helper virus.

This invention thus has many advantages over current methods for manufacturing recombinant viruses. These advantages include: (1) the nonmammalian virus backbone permits insertion of large DNA sequences without compromising the efficiency of recombinant virus production; (2) sequences normally toxic to mammalian cells (e.g., AAV rep, VSV-G, retroviral envelope proteins, eukaryotic regulatory proteins, etc.) are not expressed in substantial amounts from their mammalian regulatory sequences in the nonmammalian host cell of the nonmammalian carrier vector and thus can be tolerated by the nonmammalian carrier vector during the course of its replication in the nonmammalian host cell; (3) nonmammalian viruses do not replicate in mammalian cells, precluding contamination of the final eukaryotic vector stocks with the nonmammalian carrier vector; (4) in some embodiments no helper viruses are necessary, with the result that the final recombinant virus preparation is essentially free of helper virus; (5) frequency of wildtype virus production due to homologous or non-homologous recombination is minimized; and (6) the methods of the present invention are particularly suitable to large scale production of recombinant viruses which are themselves replication-deficient. Additionally, nonmammalian viruses are not normally pathogenic to mammalian cells, may be propagated in serum free media, and may be grown to a high titer. Other features and advantages of the invention will be apparent from the following drawings, the description of the invention and its preferred embodiments, and the examples described herein.

In one embodiment, the present invention includes nonmammalian carrier vectors containing elements that are required to produce replication-deficient recombinant viral vectors. In a preferred embodiment, the nonmammalian carrier vector contains all the elements required to produce a replication-deficient recombinant viral vector. In an even more preferred embodiment, a single nonmammalian carrier vector contains all the required elements to produce a replication-deficient recombinant viral vector. In another preferred embodiment, the nonmammalian carrier vector is a baculovirus.

In another embodiment, the invention includes a method of producing replication-deficient recombinant viral vector lysates and stocks that are free of helper or other contaminating virus. In a preferred embodiment, the method is one which is easily scaled for industrial production of recombinant viral vectors. In another preferred embodiment, the method is one in which a high titer of recombinant viral vector lysates and stocks is achieved.

In another embodiment, the invention includes attenuated, replication-competent recombinant viruses and a method of producing such viruses free of helper or other contaminating virus. In a preferred embodiment, these attenuated, replication-competent viruses may be used for immunization.

BRIEF DESCRIPTION OF THE DRAWINGS

FIGS. 2A and 2B represent a genetic map of AAV type 2. FIG. 2A is a schematic representation of the viral genome rep encodes replication proteins (Rep78, Rep68, Rep52, and Rep40) and cap encodes encapsidation functions (VP1, VP2, and VP3). Right-angled arrows: the p5, p19, and p40 viral promoters; downward vertical arrow: common polyadenylation signal upstream of the 3'-ITR FIG. 2B represents the transcripts derived from each of the three promoters. $A_n$: polyadenylation.

FIG. 6 shows the steps required for rAAV production through the use of stable cell line 293-CG3 together with one recombinant baculovirus (BV-EiOV-RC).

DETAILED DESCRIPTION OF THE INVENTION

Definitions and General Techniques

Figure 1:
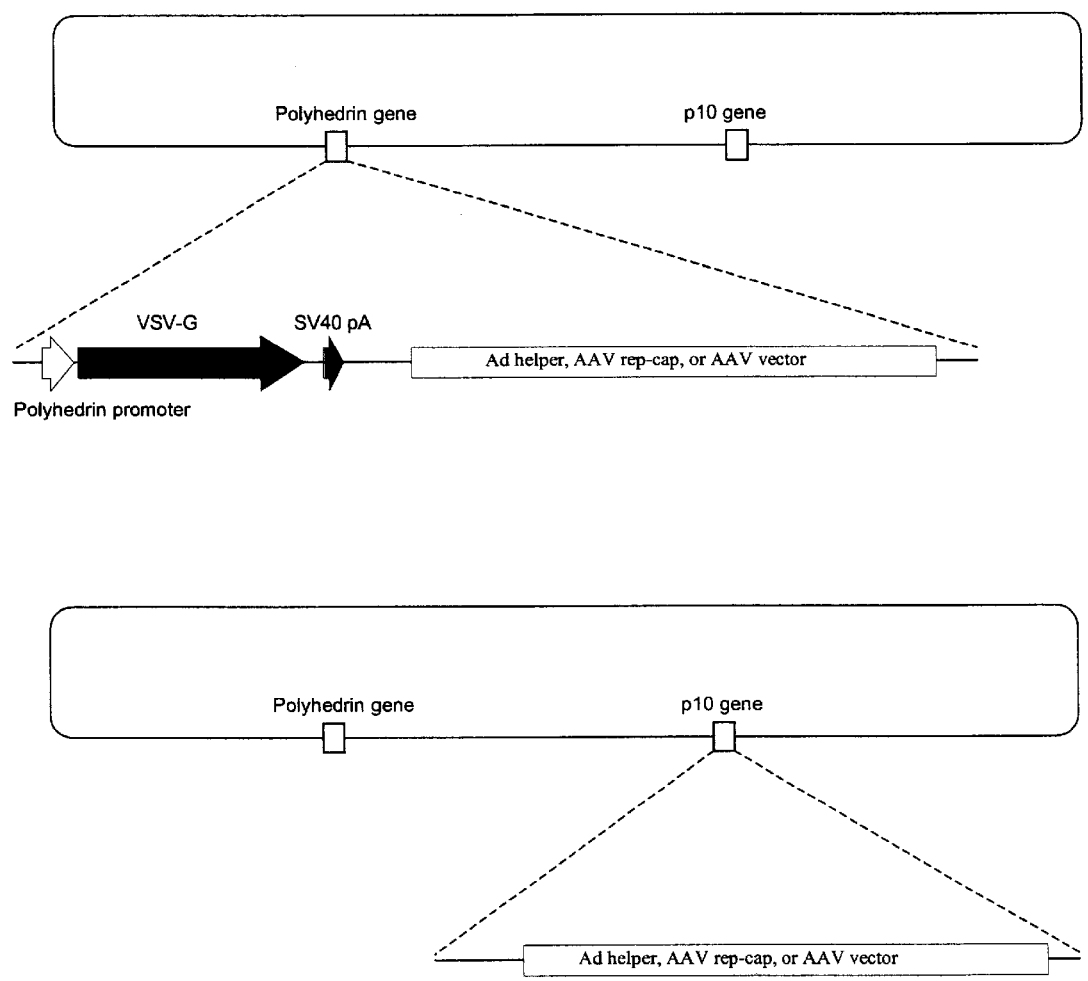
FIG. 1 is a schematic diagram of recombinant baculoviruses with target genes inserted into the loci of either polyhedrin or p10 genes.
Figure 3A:
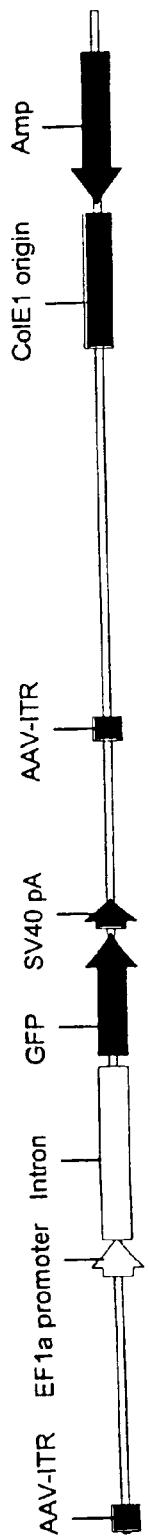
FIGS. 3A–3J are schematic diagrams of constructed plasmids used in this invention.
Figure 3B:
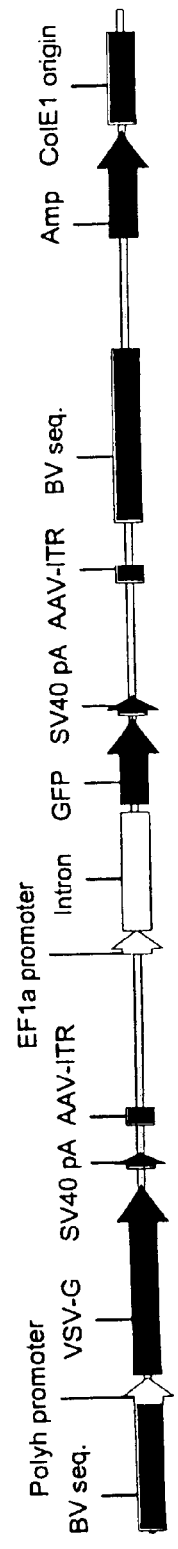
Figure 3C:
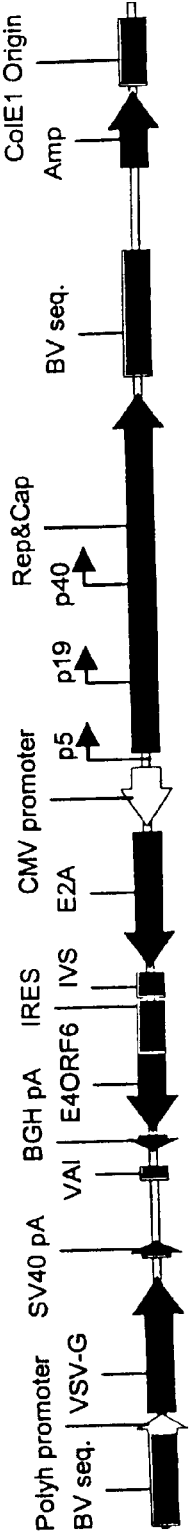
Figure 3D:
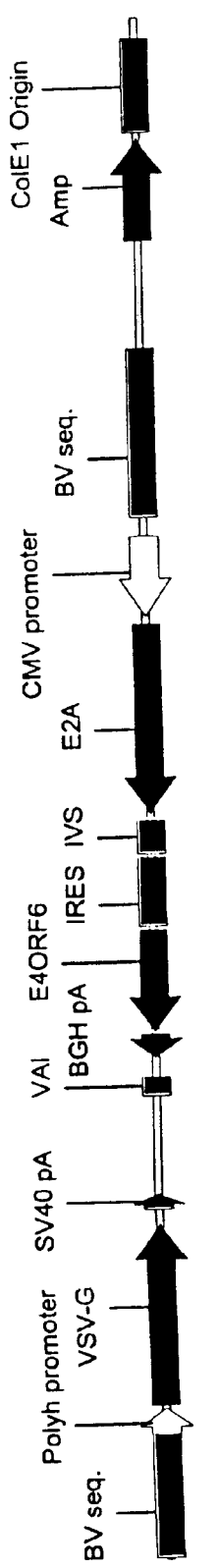
Figure 3E:
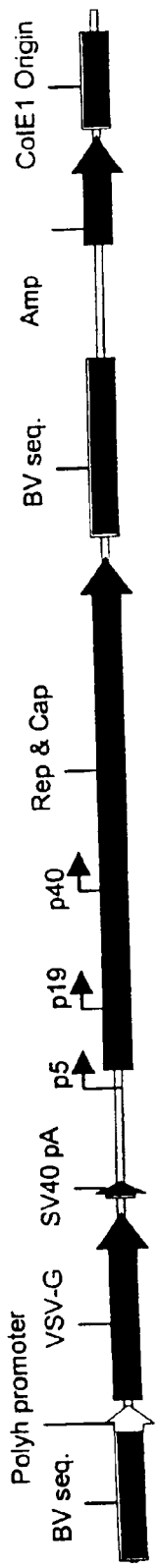
Figure 3F:
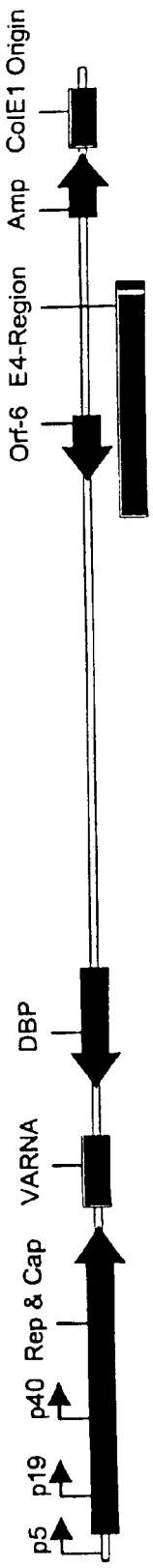
Figure 3G:
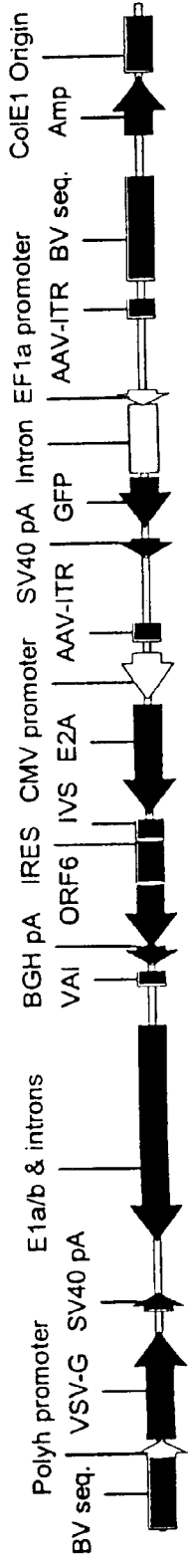
Figure 3H:
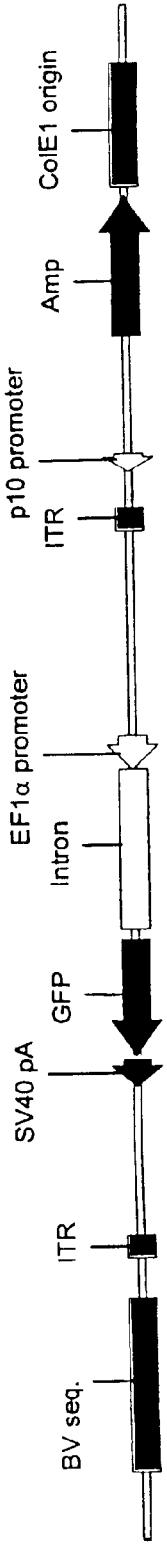
Figure 3I:
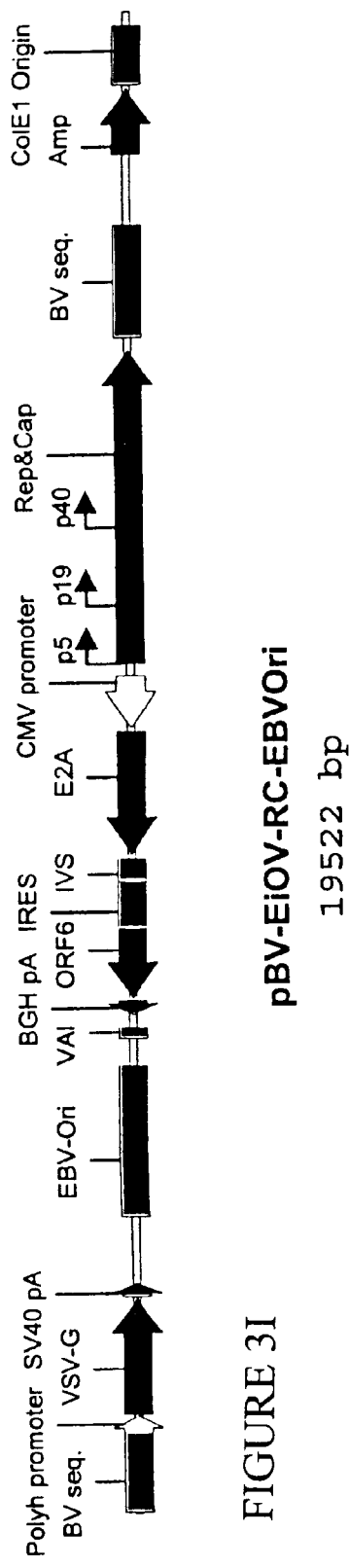
Figure 3J:
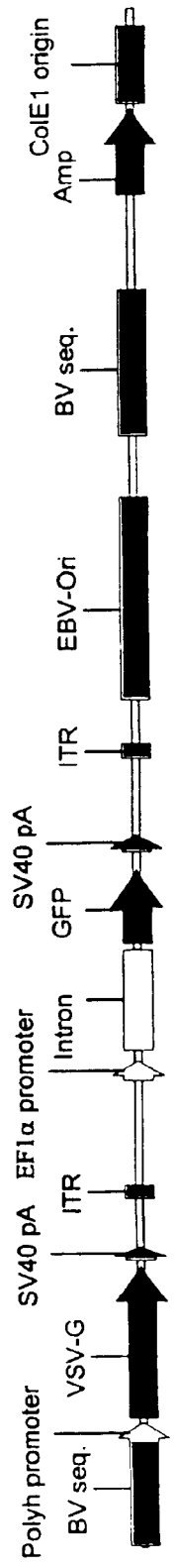
Figure 4:
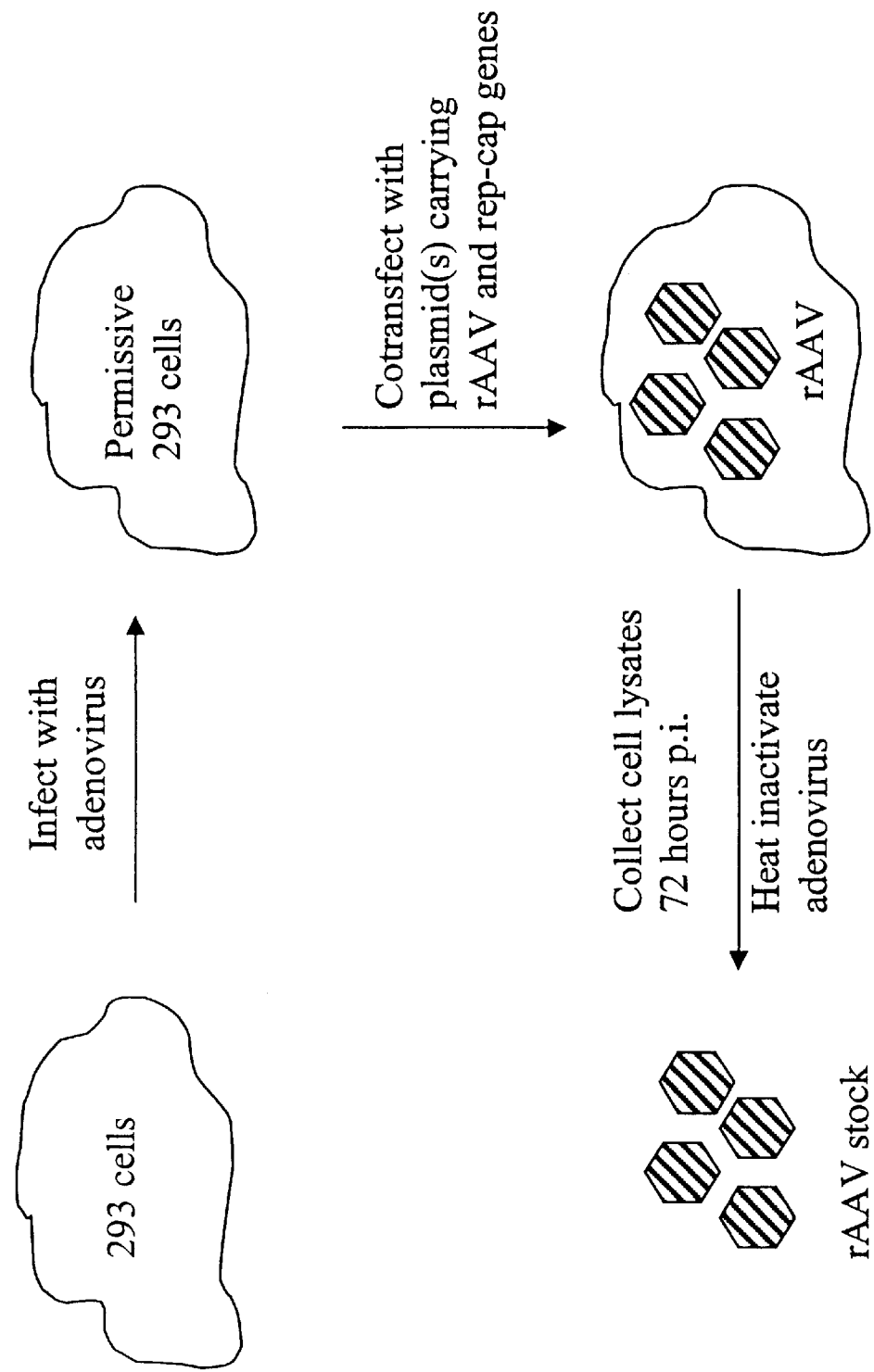
FIG. 4 shows the steps involved in rAAV production by traditional adenovirus infection/plasmid co-transfection method (Shenk et al., U.S. Pat. No. 5,436,146).
Figure 5:
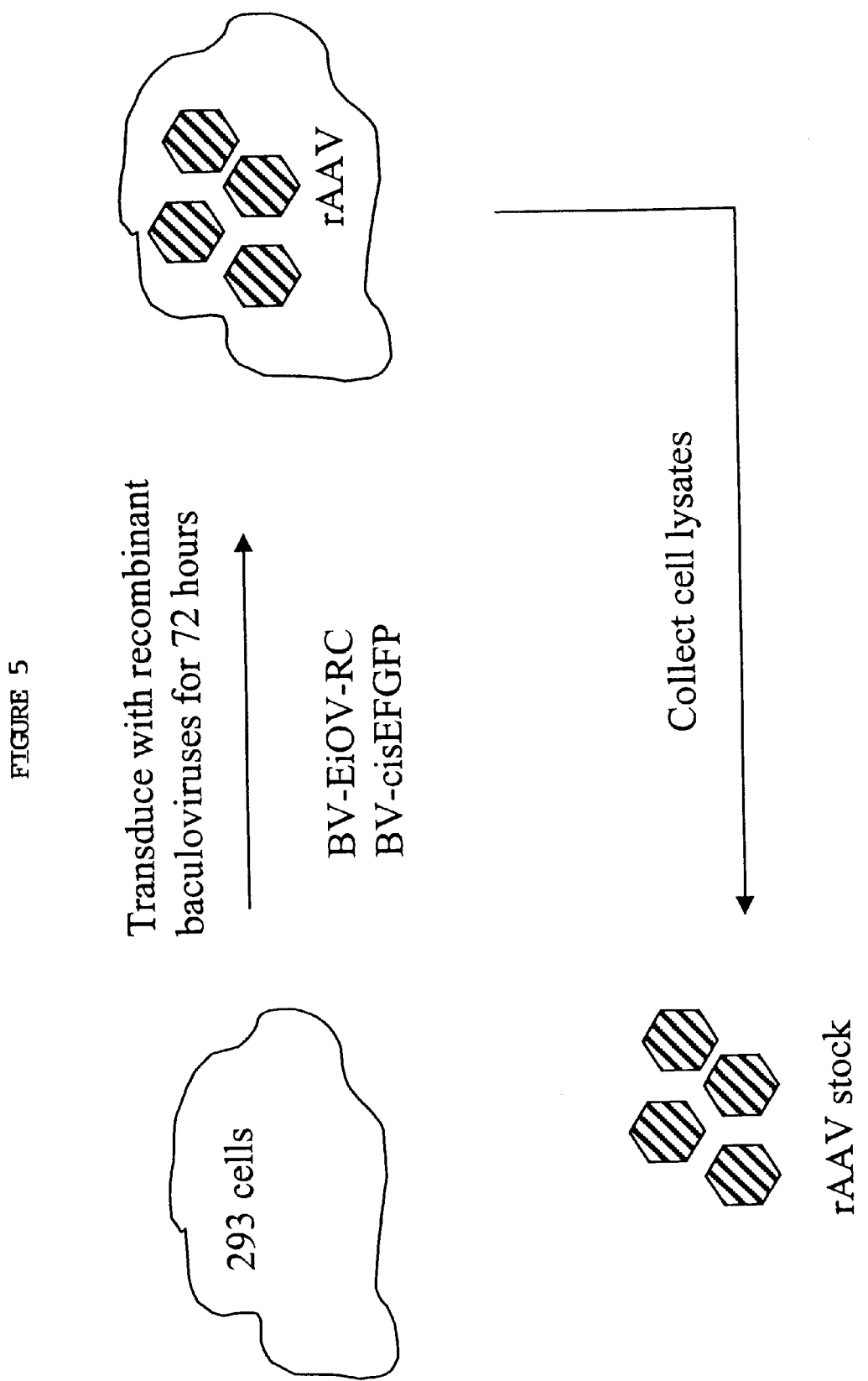
FIG. 5 shows the steps required for rAAV production through the use of two recombinant baculoviruses (BV-EiOV-RC and BV-cisEFGFP).
Figure 7:
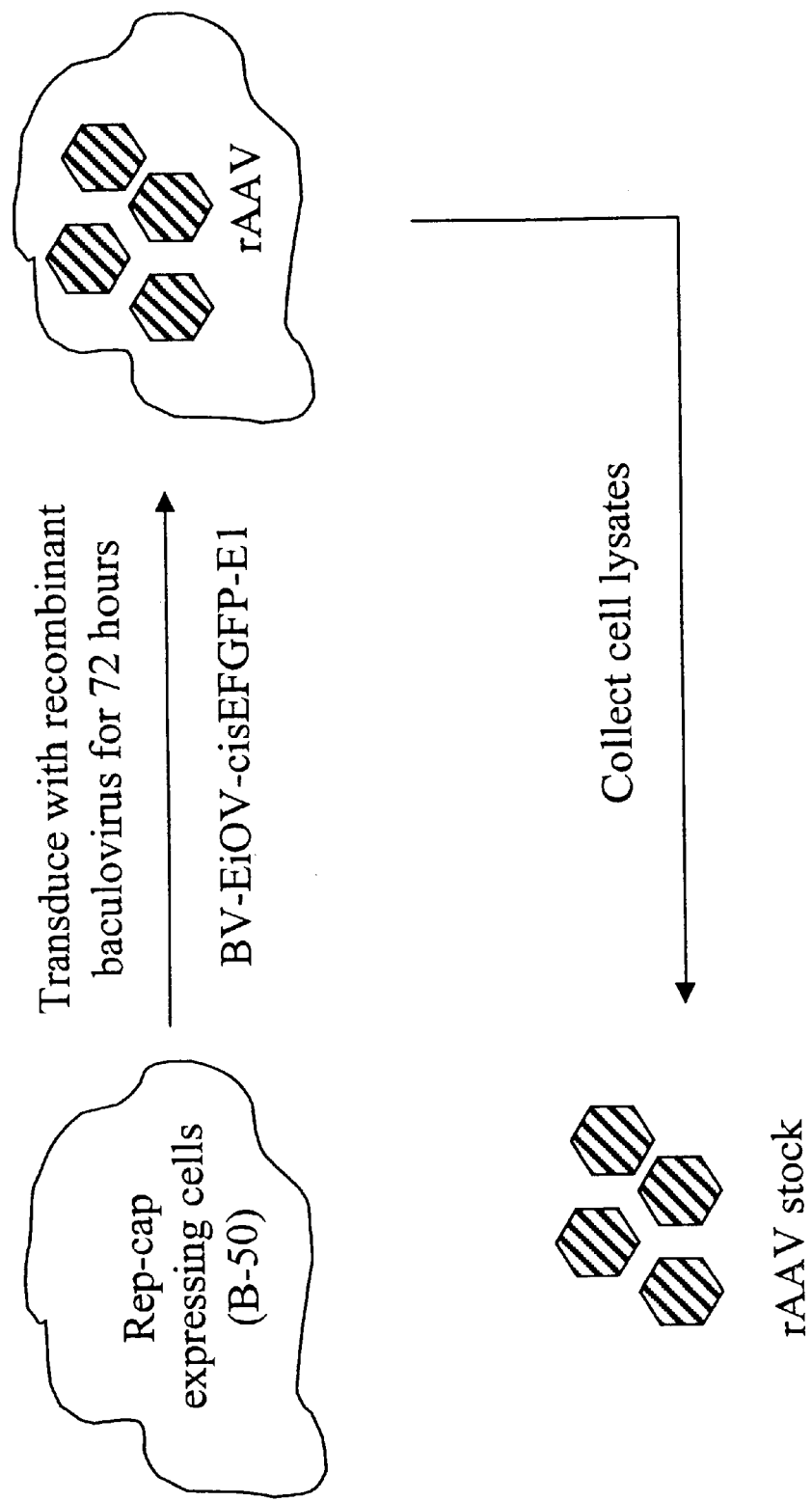
FIG. 7 shows the steps required for rAAV production through the use of stable cell line expressing AAV rep and cap genes together with recombinant baculovirus (BV-EiOV-cisEFGFP-E1).

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics, virology and immunology. See, e.g., Sambrook et al., 1989, Ausubel et al., 1992, Harlow et al. 1989 (which are incorporated herein by reference).

A "recombinant viral genome" comprises all or a part of a viral genome, wherein the viral genome may be wild type or may contain point mutations or deletions, and optionally comprises a transgene operably linked to expression control sequences. In one embodiment, the transgene is flanked by flanking elements. The recombinant viral genome of the invention is embedded in the genome of the carrier vector, and is ultimately packaged into a recombinant virus.

A "recombinant virus" is a virus derived from the recombinant viral genome described above. The recombinant virus may comprise a transgene, may be an attenuated, replication-competent virus without a transgene, may be a replication-competent virus with one or more point mutation (s), or may be a replication-deficient virus with one or more point mutations or genomic deletions, or combinations thereof The recombinant virus comprising a transgene is capable of transducing mammalian cells and delivering the transgene thereto.

A "flanking element" or "flanking nucleic acid" is a nucleic acid sequence generally derived from a mammalian virus which, when located in positions flanking a transgene, permits the packaging of the transgene into a recombinant virus. Flanking elements may be the naturally-occurring flanking elements from a mammalian virus which permit the packaging of the recombinant virus, or may be artificial nucleic acid elements, e.g. mutated sequences of flanking elements, that have the same or similar packaging function. Flanking elements include, without limitation, the inverted terminal repeats (ITRs) of AAV or Ad, the long terminal repeats (LTRs) of retrovirus, the "a" or packaging sequence of herpes simplex virus (HSV), as well as any other sequences that are required for packaging from other viruses known in the art.

A "transgene" is a nucleic acid sequence that is to be delivered or transferred to a mammalian cell. A transgene may encode a protein, peptide or polypeptide that is useful as a marker, reporter or therapeutic molecule. A transgene may also encode a protein, polypeptide or peptide that is useful for protein production, diagnostic assays or for any transient or stable gene transfer in vitro or in vivo. Alternatively, a transgene may not encode a protein but rather be used as an antisense molecule, ribozyme or other regulatory nucleic acid to inhibit replication, transcription or translation of a nucleic acid to which it is complementary or to target a complementary mRNA for degradation.

"Expression control sequences" are nucleic acid sequences that regulate the expression of a gene by being operably linked to the gene of interest. "Operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion.

As used herein, a "carrier vector" means a nucleic acid molecule comprising a nonmammalian viral nucleic acid backbone and nucleic acid sequences derived from mammalian sources, mammalian viral sources, nonmammalian sources, and nonmammalian viral sources. The nonmammalian viral nucleic acid backbone may be selected from a wide variety of sources, see, for example Table 1 of U.S. Pat. No. 5,731,182, herein incorporated by reference. The nonmammalian viral nucleic acid backbone, upon transfection of the carrier vector nucleic acid into nonmammalian cells, is sufficient to produce packaged carrier virus comprising the nucleic acid sequences inserted into the carrier vector.

A "carrier virus" is an encapsidated carrier vector capable of binding to a mammalian cell and delivering the carrier vector's genome to the cell's nucleus.

As used herein, "ligand nucleic acid" means a nucleic acid which encodes a protein which allows the carrier virus of the invention to bind to and enter a mammalian cell. The nucleic acid encoding the protein may be operably linked to expression control sequences that regulate the expression of the nucleic acid encoding the ligand.

"Helper function nucleic acid" is one or more nucleic acid sequences that encode one or more proteins, peptides or polypeptides, or that is transcribed to an RNA, wherein the one or more proteins, peptides, polypeptides or RNAs are required by certain viruses for production of recombinant viruses. The sequences may be naturally-occurring helper functions or may be sequences that have been mutated or altered but which retain their respective helper functions. The sequences may be derived from helper viruses or may be naturally-occurring or artificial nucleic acid sequences that encode non-viral proteins that act as helper functions for production of recombinant viruses. The nucleic acid sequences that are transcribed to RNA or which encode the proteins, polypeptides or peptides may be operably linked to expression control sequences that regulate the expression of the nucleic acid encoding the helper functions.

"Replication and/or encapsidation nucleic acid" is a nucleic acid sequence or sequences which encode proteins or polypeptides that are required for replication and encapsidation of the recombinant virus. The sequences may be naturally-occurring replication or encapsidation sequences or may be sequences that have been mutated or altered but which retain their respective functions of replication or encapsidation. The nucleic acid sequences encoding the proteins may be operably linked to expression control sequences that regulate the expression of the nucleic acid encoding the replication and encapsidation sequences.

A "replicon" is an episomal replication origin and those necessary proteins (or DNA encoding these proteins) to initiate nucleic acid replication.

The Carrier Vector

The carrier vector of the invention is a chimeric vector backbone derived from the nucleic acid of a nonmammalian virus. The carrier vector comprises sufficient vector sequences to be able to replicate and encapsidate within the appropriate nonmammalian host cell. The carrier vector also includes one or more of the following inserts: an embedded recombinant viral genome; a ligand nucleic acid providing for expression of a protein which can interact with a mammalian cell; replication and/or encapsidation nucleic acid required to replicate and encapsidate a recombinant virus; and helper virus functions nucleic acids.

In a preferred embodiment, the carrier vector comprises an embedded recombinant viral genome within its nonmammalian virus genomic backbone. The recombinant viral genome may comprise a transgene with associated expression regulatory sequences, wherein the transgene and regulatory sequences are bordered by flanking elements of a mammalian virus. Alternatively, the recombinant viral genome does not contain a transgene but rather contains deletions or point mutations in its sequence such that it produces an attenuated, replication-proficient recombinant virus, or other deletions or point mutations that produce a replication-deficient recombinant virus.

In a more preferred embodiment, the carrier vector comprises the embedded recombinant viral genome and either or both of 1) nucleic acid sequences encoding replication and/or encapsidation and 2) nucleic acid sequences encoding helper functions. In an even more preferred embodiment of this invention, the carrier vector additionally comprises a ligand nucleic acid providing for expression of a protein which can interact with a mammalian cell. In another preferred embodiment, the ligand nucleic acid encodes a protein which can bind to a specific mammalian cell receptor.

In the most preferred embodiment, the carrier vector comprises the embedded recombinant viral genome and all of those nucleic acid inserts required for production of a recombinant virus in a mammalian cell. For instance, if the carrier virus comprising the carrier vector is to be used to infect a cell line which expresses replication and encapsidation proteins for a recombinant AAV virus (e.g., the A64 cell line described in U.S. Pat. No. 5,658,785 and the B50 cell line described in PCT US98/19463) then the carrier vector would comprise the embedded recombinant viral genome and the helper functions, and optionally the ligand nucleic acid. Alternatively, if carrier virus is to be used to infect a cell line which expresses a helper function for a recombinant AAV virus (e.g., the 293 cell line which expresses E1), then the carrier vector would comprise the embedded recombinant viral genome, the replication and encapsidation nucleic acids for AAV (rep and cap), and the helper functions required in addition to E1 (e.g., E2a, E4ORF6 and VAI RNA), and optionally the ligand nucleic acid.

If the carrier virus is to be used to produce a recombinant retrovirus, which does not require helper functions, the carrier vector would comprise the embedded recombinant retroviral viral genome and the nucleic acids required for its replication and encapsidation (e.g., gag, pol and env) and optionally, in cases where the retrovirus is a lentivirus, one or more of the nucleic acids encoding regulatory or auxilliary proteins (e.g., tat, rev, nef, vpr, vpu). If the carrier virus is to be used to produce a recombinant retrovirus in a cell line that expresses gag, pol and env or the other functions described above in the case of lentiviruses, then the carrier virus would need only comprise the embedded recombinant retroviral genome and optionally the ligand nucleic acid. Similarly, if the carrier virus is to be used to produce a recombinant adenovirus, the carrier vector would comprise the embedded recombinant adenoviral genome and the nucleic acid sequences required for its replication and encapsidation. The type of nucleic acid sequences required for replication and encapsidation of the recombinant adenoviral genome depends upon which adenoviral genes are deleted from the recombinant adenoviral genome and whether the mammalian cell line that the carrier virus infects expresses any adenoviral genes (e.g., 293 cells express E1). Any carrier vector genome may optionally comprise a ligand nucleic acid to increase infection by the carrier virus of a mammalian cell.

The embedded recombinant viral genome and other nucleic acid inserts may be carried on separate carrier vectors, but in the most preferred embodiment, the embedded recombinant viral genome and all other desired nucleic acid inserts are carried on a single carrier vector. The advantage of a single carrier vector is that only a single infection by the carrier virus of the mammalian host cell is required in order to produce a recombinant virus.

In another embodiment of the invention, the inability of the carrier vector to replicate in mammalian cells is overcome by supplying a mammalian replicon to the carrier vector. The provision of a replicon assures that mammalian cells infected by the carrier vector maintain a sufficient copy number of the carrier vector extrachromosomally throughout a population of proliferating and dividing mammalian cells.

Based on this description, other embodiments of the carrier vector will be readily apparent to those of ordinary skill in the art.

Nonmammalian Virus Backbone

The chimeric carrier vector is constructed from a backbone of a nonmammalian virus. The backbone need not be the entire genome of the nonmammalian virus, but may be only that portion of the genome necessary for replication in a nonmammalian host. Preferably, the vector backbone is derived from an invertebrate virus. Table 1 of U.S. Pat. No. 5,731,182 lists several examples of viruses that may be used to form the backbone of the chimeric vector, the sequences of which are available from various sources, such as Genbank. In a preferred embodiment, the invertebrate DNA virus is a baculovirus. In a more preferred embodiment, the bacuolovirus is a Granulovirus or Nucleopolyhedrovirus. In an even more preferred embodiment, the nonmammalian viral backbone is derived from the baculovirus *Autographa californica* nuclear polyhedrosis virus (AcNPV). See, e.g., GenBank Accession No. L22858.

In a preferred embodiment, the nonmammalian virus backbone must be capable of replication in its ordinary host cell, but incapable of replication in a mammalian cell. For example, the baculovirus virus backbone exemplified herein replicates only in insect cells.

The Embedded Recombinant Viral Genome

The methods of the present invention allow for large scale production of high titers of recombinant virus, i.e., one that has a transgene inserted therein to be delivered to target mammalian cells, or one that does not have a transgene but rather has a mutation or deletion in a viral gene and is to be used as a vaccine, e.g., an attenuated and replication-proficient recombinant virus or a replication-deficient mutant virus. The recombinant virus may be any virus of interest for use to deliver transgenes to mammalian cells or for use as a vaccine. Preferred recombinant viruses for delivery of a transgene include adenoviruses, retroviruses, adeno-associated viruses, herpesvirus amplicons and hepatitis B viruses.

In order to manufacture a recombinant virus containing a transgene, the method of the present invention begins with a desired transgene, then associates the transgene with appropriate expression regulatory sequences (ERS), e.g., promoter, enhancer, polyadenylation site, then inserts this ERS-transgene construct between the packaging elements of the virus to be manufactured, in place of the genes normally found therein. Where the length of the replacement is shorter than that being replaced, and that shorter length would pose an obstacle to proper packaging, an optional spacer or "stuffer" sequence may be inserted in order to maintain the proper length for packaging. The entire construct of the ERS-transgene constructed bordered by the flanking elements is the genome of the recombinant virus of the present invention, which is then embedded in the carrier vector's genome, at which point it subsists as an embedded recombinant viral genome. Each of these elements is described in detail below:

The Transgene

The composition of the transgene sequence depends upon the intended use for the resulting recombinant virus. For example, one type of transgene sequence comprises a reporter or marker sequence, which upon expression produces a detectable signal. Such reporter or marker sequences include, without limitation, DNA sequences encoding *E. coli* β-lactamase, β-galactosidase (LacZ), alkaline phosphatase, HSV thymidine kinase, green fluorescent protein (GFP), bacterial chloramphenicol acetyltransferase (CAT), firefly luciferase, eukaryotic membrane bound proteins including, for example, CD2, CD4, CD8, the influenza hemagglutinin protein, and others well known in the art, to which high affinity antibodies directed to them exist or can be made routinely, and fusion proteins comprising a membrane bound protein appropriately fused to an antigen tag domain from, among others, hemagglutinin or myc.

These sequences, when associated with regulatory elements which drive their expression, provide signals detectable by conventional means, including enzymatic, radiographic, calorimetric, fluorescence or other spectroscopic assays, fluorescent activated cell sorting assay and immunological assays, including ELISA, RIA and immunohistochemistry. For example, where the transgene is the LacZ gene, the presence of a recombinant virus is detected by assays for β-galactosidase activity. Similarly, where the transgene is luciferase, the recombinant virus gene expression may be measured by light production in a luminometer.

However, desirably, the transgene is a non-marker gene which can be delivered to a cell or an animal via the recombinant virus produced by this method. The transgene may be selected from a wide variety of gene products useful in biology and medicine, such as proteins, antisense nucleic acids (e.g., RNAs), or catalytic RNAs. The invention may be used to correct or ameliorate gene deficiencies, wherein normal genes are expressed but at less than normal levels, and may also be used to correct or ameliorate genetic defects wherein a functional gene product is not expressed. A preferred type of transgene sequence is a therapeutic gene which expresses a desired corrective gene product in a host cell. These therapeutic nucleic acid sequences typically encode products which, upon expression, are able to correct, complement or compensate an inherited or non-inherited genetic defect, or treat an epigenetic disorder or disease. However, the selected transgene may encode any product desirable for study. The selection of the transgene sequence is not a limitation of this invention. Choice of a transgene sequence is within the skill of the artisan in accordance with the teachings of this application.

The invention also includes methods of producing recombinant virus and compositions thereof which can be used to correct or ameliorate a gene defect caused by a multi-subunit protein. In certain situations, a different transgene may be used to encode each subunit of the protein. This may be desirable when the size of the DNA encoding the protein subunit is large, e.g., for an immunoglobulin or the platelet-derived growth factor receptor. In order for the cell to produce the multi-subunit protein, a cell would be infected with recombinant virus expressing each of the different subunits.

Alternatively and more preferably, different subunits of a protein may be encoded by the same transgene. In this case, a single transgene would include the DNA encoding each of the subunits, with the DNA for each subunit separated by an internal ribosome entry site (IRES). The use of IRES permits the creation of multigene or polycistronic mRNAs. IRES elements are able to bypass the ribosome scanning model of 5' methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian mRNA (Macejak and Sarnow, 1991). IRES elements can be linked to heterologous open reading frames. By virtue of the IRES element, each open reading frame is accessible to ribosomes for efficient translation. Thus, multiple genes can be efficiently expressed using a single promoter/enhancer to transcribe a single message. This is preferred when the size of the DNA encoding each of the subunits is sufficiently small that the total of the DNA encoding the subunits and the IRES is no greater than the maximum size of the DNA insert that the virus can encompass. For instance, for rAAV, the insert size can be no greater than approximately 4.8 kilobases, however, for an adenovirus which lacks all of its helper functions, the insert size is approximately 28 kilobases.

Useful gene products include hormones and growth and differentiation factors including, without limitation, insulin, glucagon, growth hormone (GH), parathyroid hormone (PTH), calcitonin, growth hormone releasing factor (GRF), thyroid stimulating hormone (TSH), adrenocorticotropic hormone (ACTH), prolactin, melatonin, vasopressin, β-endorphin, met-enkephalin, leu-enkephalin, prolactin-releasing factor, prolactin-inhibiting factor, corticotropin-releasing hormone, thyrotropin-releasing hormone (TRH), follicle stimulating hormone (FSH), luteinizing hormone (LH), chorionic gonadotropin (CG), vascular endothelial growth factor (VEGF), angiopoietins, angiostatin, endostatin, granulocyte colony stimulating factor (GCSF), erythropoietin (EPO), connective tissue growth factor (CTGF), basic fibroblast growth factor (bFGF), bFGF2, acidic fibroblast growth factor (aFGF), epidermal growth factor (EGF), transforming growth factor a (TGFα), platelet-derived growth factor (PDGF), insulin-like growth factors I and II (IGF-I and IGF-II), any one of the transforming growth factor β (TGFβ) superfamily comprising TGFβ, activins, inhibins, or any of the bone morphogenic proteins (BMP) BMPs 1–15, any one of the heregulin/neuregulin/ARIA/neu differentiation factor (NDF) family of growth factors, nerve growth factor (NGF), brain-derived neurotrophic factor (BDNF), neurotrophins NT-3, NT-4/5 and NT-6, ciliary neurotrophic factor (CNTF), glial cell line derived neurotrophic factor (GDNF), neurtuin, persephin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-1β, IL-2, IL-3, IL-4, IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), granulocyte colony stimulating factor (G-CSF), monocyte colony stimulating factor (M-CSF), Fas ligand, tumor necrosis factors α and β (TNFα and TNFβ), interferons (IFN) IFN-α, IFN-β and IFN-γ, stem cell factor, flk-2/flt3 ligand. Gene products produced by the immune system are also encompassed by this invention. These include, without limitations, immunglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Useful gene products also include complement regulatory proteins such as membrane cofactor protein (MCP), decay accelerating factor (DAF), CR 1, CR2 and CD59.

Still other useful gene products include any one of the receptors for the hormones, growth factors, cytokines, lymphokines, regulatory proteins and immune system proteins. Examples of such receptors include flt-1, flk-1, TIE-2; the trk family of receptors such as TrkA, MuSK, Eph, PDGF receptor, EGF receptor, HER2, insulin receptor, IGF-1 receptor, the FGF family of receptors, the TGFβ receptors, the interleukin receptors, the interferon receptors, serotonin receptors, α-adrenergic receptors, β-adrenergic receptors, the GDNF receptor, p75 neurotrophin receptor, among others. The invention encompasses receptors for extracellular matrix proteins, such as integrins, counter-receptors for transmembrane-bound proteins, such as intercellular adhesion molecules (ICAM-1, ICAM-2, ICAM-3 and ICAM-4), vascular cell adhesion molecules (VCAM), and selectins E-selectin, P-selectin and L-selectin. The invention encompasses receptors for cholesterol regulation, including the LDL receptor, HDL receptor, VLDL receptor, and the scavenger receptor. The inventions encompasses the apolipoprotein ligands for these receptors, including ApoAI, ApoAIV and ApoE. The invention also encompasses gene products such as steroid hormone receptor superfamily including glucocorticoid receptors and estrogen receptors, Vitamin D receptors and other nuclear receptors. In addition, useful gene products include antimicrobial peptides such as defensins and maginins, transcription factors such as jun, fos, max, mad, serum response factor (SRF), AP-1, AP-2, myb, MRG1, CREM, Alx4, FREAC1, NF-κB, members of the leucine zipper family, C2H4 zinc finger proteins, including Zif268, EGR1, EGR2, C6 zinc finger proteins, including the glucocorticoid and estrogen receptors, POU domain proteins, exemplified by Pit1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor 1 (IRF-1), Wilms tumor protein, ETS-binding protein, STAT, GATA-box binding proteins, e.g., GATA-3, and the forkhead family of winged helix proteins.

Other useful gene products include carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, porphobilinogen deaminase, factor VII, factor VIII, factor IX, factor II, factor V, factor X, factor XII, factor XI, von Willebrand factor, superoxide dismutase, glutathione peroxidase and reductase, heme oxygenase, angiotensin converting enzyme, endothelin-1, atrial natriuetic peptide, pro-urokinase, urokinase, plasminogen activator, heparin cofactor II, activated protein C (Factor V Leiden), Protein C, antithrombin, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), the product of Wilson's disease gene PWD, Cu/Zn superoxide dismutase, aromatic aminoacid decarboxylase, tyrosine hydroxylase, acetylcholine synthetase, prohormone convertases, protease inhibitors, lactase, lipase, trypsin, gastrointestinal enzymes including chyromotrypsin, and pepsin, adenosine deaminase, α1 anti-trypsin, tissue inhibitor of metalloproteinases (TLMP), GLUT-1, GLUT-2, trehalose phosphate synthase, hexokinases I, II and III, glucokinase, any one or more of the individual chains or types of collagen, elastin, fibronectin, thrombospondin, vitronectin and tenascin, and suicide genes such as thymidine kinase and cytosine deaminase.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other useful proteins include truncated receptors which lack their transmembrane and cytoplasmic domain. These truncated receptors can be used to antagonize the function of their respective ligands by binding to them without concomitant signaling by the receptor. Other types of non-naturally occurring gene sequences include antisense molecules and catalytic nucleic acids, such as ribozymes, which could be used to reduce overexpression of a gene.

Other useful transgenes include those that encode antigenic peptides capable of generating an immune response. Recombinant vectors comprising these transgenes can be used for genetic immunization. Useful transgenes include those that encode peptides specific for Epstein Barr virus; HIV; simian immunodeficiency virus (SIV); human T-cell leukemia viruses I and II (HTLV-I and HTLV-II); hepatitis A, B, C, D and E; pseudorabies virus; rabies virus; cytomegalovirus; respiratory syncytial virus; parainfluenza virus types 1–4; mumps virus; rubella virus; polio virus; rubeola virus; influenza virus types A, B and C; rotavirus; herpes simplex viruses types 1 and 2; varicella-zoster virus; human herpes virus type 6; hantavirus; adenoviruses; chlamydia pneumoniae; chlamydia trachomatis; mycoplasma pneumoniae; mycobacterium tuberculosis; atypical mycobacteria; feline leukemia virus; feline immunodeficiency virus; bovine immunodeficiency virus; equine infectious anemia virus; caprine arthritis encephalitis virus, visna virus; Staphlococcus species and Streptococcus species. The transgenes may also be directed against peptides from tumor antigens to provide immunization for tumors and cancers.

Expression Control Sequences

A great number of expression control sequences—native, constitutive, inducible and/or tissue-specific—are known in the art and may be utilized to drive expression of the transgene and the nucleic acid sequences encoding the replication and encapsidation functions of the recombinant virus, the helper functions and the ligand. The choice of expression control sequence depends upon the type of expression desired. For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' flanking sequence of the transgene. A transgene-carrying molecule useful in the present invention may also contain an intron, desirably located between the promoter/enhancer sequence and the transgene. One possible intron sequence is also derived from SV-40, and is referred to as the SV-40 T intron sequence. Another vector element that may be used is an internal ribosome entry site (IRES), as described above. An IRES sequence is used to produce more than one polypeptide from a single gene transcript. An IRES sequence can be used for the transgene or for any of the other nucleic acid sequences encoding the replication and encapsidation polypeptides, the helper functions or the ligand. Selection of these and other common vector elements are conventional and many such sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer [see, e.g., Boshart et al, *Cell*, 41:521–530 (1985)], the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system [WO 98/10088]; the ecdysone insect promoter [No et al, *Proc. Natl. Acad. Sci. USA*, 93:3346–3351 (1996)]; the tetracycline-repressible system [Gossen et al, *Proc. Natl. Acad. Sci. USA*, 89:5547–5551 (1992)]; the tetracycline-inducible system [Gossen et al., *Science*, 268:1766–1769 (1995); see also Harvey et al., *Curr. Opin. Chem. Biol.*, 2:512–518 (1998)]; the RU486-inducible system [Wang et al., *Nat. Biotech.*, 15:239–243 (1997) and Wang et al., *Gene Ther.*, 4:432–441 (1997)]; and the rapamycin-inducible system [Magari et al., *J. Clin. Invest.*, 100:2865–2872 (1997); Rivera et al., *Nat. Medicine.* 2:1028–1032 (1996)]. Other types of inducible promoters which may be useful in this context are those which are regulated by a specific physiological state, e.g., temperature, acute phase, or in replicating cells only. In a preferred embodiment, the transgene is under the control of the native p5 promoter of AAV.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter. For instance, if expression in skeletal muscle is desired, a promoter active in muscle may be used. These include the promoters from genes encoding skeletal a-actin, myosin light chain 2A, dystrophin, muscle creatine kinase, as well as synthetic muscle promoters with activities higher than naturally-occurring promoters [see Li et al., *Nat. Biotech.*, 17:241–245 (1999)]. Examples of promoters that are tissue-specific are known for liver [albumin, Miyatake et al. *J. Virol.*, 71:5124–32 (1997); hepatitis B virus core promoter, Sandig et al., *Gene Ther*. 3:1002–9 (1996); alphafetoprotein (AFP), Arbuthnot et al., *Hum. Gene Ther.*, 7:1503–14 (1996)], bone [osteocalcin, Stein et al., *Mol. Biol. Rep.*, 24:185–96 (1997); bone sialoprotein, Chen et al., *J. Bone Miner. Res.* 11 :654–64 (1996)], lymphocytes [CD2, Hansal et al., *J. Immunol.*, 161:1063–8 (1998); immunoglobulin heavy chain; T cell receptor a chain], neuronal [neuron-specific enolase (NSE) promoter, Andersen et al. *Cell. Mol. Neurobiol.*, 13:503–15 (1993); neurofilament light-chain gene, Piccioli et al., *Proc. Natl. Acad. Sci. USA*, 88:5611–5 (1991); the neuron-specific vgfgene, Piccioli et al., *Neuron*, 15:373–84 (1995)]; among others.

Of course, not all vectors and expression control sequences will function equally well to express all of the transgenes or other nucleic acid sequences of this invention. However, one of skill in the art may make a selection among these expression control sequences without departing from the scope of this invention. Suitable promoter/enhancer sequences which function in the appropriate host cell of choice may be selected by one of skill in the art using the guidance provided by this application. Such selection is a routine matter and is not a limitation of the molecule or construct.

In one method of identifying a suitable expression control sequence for a desired nucleic acid sequence, one may select one or more expression control sequences and operably link the expression control sequence to the nucleic acid sequence to be regulated. Then, one may insert these operably linked sequences comprising the expression control sequence and regulated sequence into the genome of the carrier vector. In one embodiment, one may insert a recombinant viral genome comprising the expression control sequence and the transgene into a nonmammalian vector of the instant invention. After following one of the methods for producing and packaging the recombinant vector as taught in this specification one may infect suitable cells in vitro or in vivo. The number of copies of the transgene in the cell may be monitored by Southern blotting or quantitative PCR; the level of RNA expression may be monitored by Northern blotting or quantitative RT-PCR; and the level of protein expression may be monitored by Western blotting, immunohistochemistry, ELISA, RIA, tests of the transgene's gene product's biological activity, either in vitro or in vivo, or tests for correction or amelioration of a genetic defect.

In a similar fashion, one may select one or more expression control sequences and operably link it to a nucleic acid sequence encoding replication and encapsidation proteins, helper functions or a ligand, and insert the resultant desired nucleic acid molecule into a vector of the instant invention. One may also select one or more vector replication sequences and insert them into a vector of the instant invention. After packaging and infecting nonmammalian cells, one may measure the particular effects, e.g., on expression of the ligand or on replication of the vector, by one of the methods described above. One may also use a functional test to determine if one or more particular expression control sequences operably linked to a nucleic acid sequence encoding a ligand produces a carrier virus which is able to infect mammalian cells efficiently. One may assay a number of different expression control sequences to determine which one is most effective for mammalian cell infection. The same may be done using a variety of vector replication sequences.

Furthermore, after infecting mammalian host cells and obtaining recombinant virus, one may infect mammalian cells with the recombinant virus, then measure the expression of the replication and encapsidation proteins and/or helper functions by one of the methods described above. One may also use a functional test to determine if one or more particular expression control sequences operably linked to one or more helper functions or replication or encapsidation functions is capable of supporting production of a infectious recombinant virus. One may determine which of many expression control sequences are most effective in producing a high titer of infectious recombinant virus.

Flanking Elements

Flanking elements are required for replication, excision and packaging of many viruses, and each type of virus has its own type of flanking elements. In a wild-type virus, these elements flank the viral genes when the viral DNA integrates in to a host cell chromosome. In the case of integrating viruses, when the wild-type virus is rescued from the host chromosome, the flanking elements excise along with the viral DNA and remain in flanking positions surrounding the rescued viral DNA, in a form suitable for packaging into virions. For non-integrating, extrachromosomal viruses (e.g. HSV), flanking sequences serve functions in DNA replication and packaging. In recombinant viruses, much or all of the viral nucleic acid sequences between the flanking elements are removed from the virus and are replaced with a transgene and its associated expression regulatory sequences.

In one embodiment of the invention, the recombinant virus is a recombinant adenovirus, and comprises a selected transgene operably linked to expression regulatory sequences and the adenoviral flanking elements. Adenoviral flanking elements are ITRs and are 100–200 bp in length. A large number of adenoviral flanking elements are known, such as those from human adenoviruses types 1–46, chimpanzee adenoviruses, canine adenoviruses, bovine adenoviruses [all available from the American Type Culture Collection (ATCC), 10801 University Boulevard, Manassas, Va. 20110–2209].

In another embodiment, the recombinant virus is a recombinant retrovirus, and comprises a selected transgene operably linked to expression regulatory sequences and retroviral flanking elements. The flanking elements are long terminal repeat (LTR) sequences that are present at the 5' and 3' ends of the retroviral genome. These LTRs contain strong promoter and enhancer sequences and are also required for integration in the host cell genome (Coffin, 1990). A large number of retroviral LTRs are known. See, for instance, U.S. Pat. No. 5,672,510.

In yet another embodiment of the invention, the recombinant virus is a recombinant AAV, and comprises a selected transgene operably linked to expression regulatory sequences and AAV flanking elements. The naturally-occurring AAV ITRs consist of approximately 145 bp at the 5' and 3' ends of the AAV genome. The AAV ITRs are required for replication, excision and encapsidation of both wild type and recombinant AAV virions.

In another embodiment, the recombinant virus is either a herpesvirus derivative containing one or more mutations or deletions of viral genes, or is a herpesvirus amplicon. In either case, the flanking elements would be the viral terminal repeats (e.g., the "a" sequence if the virus is HSV). HSV amplicons are defective HSV genomes containing the packaging sequence (a), viral origin of DNA replication (ori) and the transgene cassette of interest operably linked to the desired expression regulatory sequences. In the presence of helper herpesvirus or substitute helper functions, the amplicon is replicated and packaged as head-to-tail concatemers to form wild-type size genomes.

In another embodiment, the recombinant virus is a recombinant defective hepatitis B virus (HBV) and comprises a selected transgene operably linked to expression regulatory sequences and inserted into the HBV genome. In vitro studies have shown that the recombinant hepatitis B virus retains the ability for helper-dependent packaging and reverse transcription despite the deletion of up to 80% of its genome (Horwich et al., 1990). This suggests that large portions of the genome may be replaced with foreign genetic material. The hepatotropism and persistence (integration) were particularly attractive properties for liver-directed gene transfer.

Ligand DNA

Most nonmammalian viruses are not infectious to mammalian cells; however, it has been reported that in some cases, nonmammalian viruses will infect certain particularly infection-susceptible mammalian cell lines. [Barsoum et al., Human Gene Therapy 8:2011–2018 (Nov. 20, 1997)]. Where the host cell to be used for manufacturing the recombinant virus is not susceptible to infection by the nonmammalian virus, the nonmammalian virus may be modified by incorporating ligand DNA in the nonmammalian backbone. The nonmammalian backbone may also be modified by incorporation of ligand DNA to increase infection of mammalian host cell by the nonmammalian virus. The expression of the ligand DNA by the subsequently produced nonmammalian virus will permit infection or increase infection of mammalian cells. The backbone of the carrier vector of the present invention is modified by addition of DNA encoding components needed to produce a ligand which is recognized by a desired mammalian cell.

The ligand DNA is selected from genes which, when expressed, yield a gene product that will be present on the surface of the encapsidated carrier vector, thus presenting the ligand to the mammalian cell target receptors and allowing the carrier vector to bind to and enter mammalian cells. [Barsoum et al., Human Gene Therapy 8:2011–2018 (Nov. 20, 1997).] The ligand DNA is placed under the regulatory control of expression regulatory sequences that insure that the ligand gene product is expressed coordinately with the replicated DNA of the carrier vector to allow efficient chimeric carrier vector production in nonmammalian host cells. The nonmammalian expression regulatory sequence may be identical, similar, or distinct from the backbone's native regulatory sequences, so long as it is capable of regulatory functions in the nonmammalian host cell. In a preferred embodiment, the expression regulatory sequences comprise a promoter derived from the native nonmammalian virus from which the nonmammalian vector backbone is derived. In a more preferred embodiment, the promoter is polyhedrin early promoter (polH) and the nonmammalian vector backbone is derived from baculovirus.

In general, if a ligand DNA is regulated by nonmammalian expression regulatory sequences, the ligand DNA will not be expressed when the chimeric vector infects the mammalian host cell. The absence of expression of the ligand encoded by the DNA may be useful to prevent incorporation of ligand into the recombinant virus coat encoded from the carrier nonmammalian vector, which could disrupt its structural integrity or cause adverse immunogenic reactions in an animal. However, if ligand expression is desired in the mammalian host cell, then alternative or additional expression regulatory sequences may be operably linked to the sequences encoding the ligand to permits its expression in mammalian and nonmammalian host cells. Alternatively, there may be some instances in which the ligand DNA is expressed because the nonmammalian expression regulatory sequences are also activated in the mammalian cells.

The ligand DNA can be essentially any nucleic acid that encodes a protein, polypeptide or peptide that modifies the mature nonmammalian virus to enable it to bind to and enter mammalian cells. The ligand can be naturally-occurring protein, a fragment of a naturally-occurring protein that has a desired binding capability, or an artificial or mutated polypeptide or peptide that has a desired binding capability. The ligand can be one of general specificity, which would allow binding to a wide variety of mammalian cells (e.g., vesicular stomatitis virus glycoprotein G (VSV-G) gene, bovine syncytial virus (BSV) envelope glycoprotein gene, or amphotropic envelope gene as illustrated below), or it may be more specific, allowing binding to targeted specific cell types. For instance, the ligand may cause the virus to bind via electrostatic interactions or other general mechanism of interacting the mammalian cell, or it may be a specific ligand-receptor interaction.

Useful ligand nucleic acids may be any nucleic acid which encodes a ligand that permits the nonmammalian virus to interact with the mammalian cell. For instance, the ligand may be one which increases the electrostatic interaction between the virus and the mammalian cell for a receptor found on the mammalian host cells that are to be infected by the carrier virus. Other useful ligand nucleic acids include, without limitation, nucleic acids encoding peptide hormones, growth factors, or other normally secreted factors for which the mammalian host cell of interest expresses a receptor. The nucleic acids useful as a ligand include all those secreted factors, peptide hormones and growth factors which have a normal cellular receptor and which are disclosed above for transgenes. For instance, the ligand nucleic acid may encode PDGF, EGF, bFGF, aFGF, insulin, IGF-I, IGF-II, apoE, apoA1, apoA4, EPO, PTH, GH or GRF. The ligand nucleic acid may encode a native or genetically engineered immunoglobulin (e.g., ScFv, chimeric immunoglobulin, humanized immunoglobulin, etc.) or MHC molecule that specifically binds to a particular cell surface protein on the mammalian cell. Other ligand nucleic acids of interest encode a member of the extracellular matrix such as a collagen, elastin, thrombospondin, tenascin or vitronectin, which bind to integrins and other cellular transmembrane receptors. The nucleic acid sequence encoding a ligand which is normally secreted may be modified by incorporating a nucleic acid sequence encoding an "anchoring domain" at either the 5' or 3' end of the coding sequence for the ligand. The anchoring domain is a region that secures the ligand in the viral coat. In a preferred embodiment, the :anchoring domain is at the 3' end of the coding sequence for the ligand. In a further preferred embodiment, the anchoring domain is derived from a viral coat protein, such as HIV gp41 (which anchors gp 120 coat protein to the viral envelope). Other examples include E protein of dengue virus or the 14 kDa protein of vaccinia virus.

The ligand nucleic acid also may encode a protein that is normally anchored in the cell membrane of a mammalian cell which binds to a particular cell surface protein or counter-receptor on a mammalian host cell. Examples of this type of ligand nucleic acid include a number of the CD antigens, such as the T cell receptor (TCR), CTLA-4 receptor and B-7, integrins such as Mac-1, LFA-1, and p150,95, intercellular adhesion molecules such as ICAM-1, ICAM-2, ICAM-3 and ICAM-4, and selecting, such as E-selectin, P-selectin and L-selectin. The ligand may also be an artificial or mutated counter-receptor, such as a cell-surface anchored or hybrid immunoglobulin or TCR.

In one embodiment, the ligand is one that is normally present on a virus and which mediates binding to a mammalian cell, for example, gp120 of HIV or HA from influenza. In another embodiment, the ligand is one that is normally present on a bacterial cell and which mediates binding to a mammalian cell, for example, Protein A from *Staphylococcus aureus* is known to bind to immunoglobulins.

In another embodiment, the mammalian host cell is genetically engineered to express a receptor which specifically binds to a ligand. Thus, one can design mammalian host cell-carrier virus systems that promote highly specific binding of the carrier virus to the mammalian host cell. For example, one may engineer a mammalian host cell line to express a growth factor receptor, such as the EPO receptor, and design the carrier vector to comprise a ligand nucleic acid comprising the EPO gene. One of skill in the art, in light of the instant specification, would be able to identify a large number of mammalian host cell-carrier virus interactive receptor-ligand systems.

In one embodiment the ligand DNA is the VSV-G gene. This gene may be placed under the control of the baculovirus polyhedrin (pPH) early promoter. The VSV-G protein, when expressed, modifies the mature carrier virus such that it may bind to mammalian host cells and thereby infect them. [Barsoum, supra]. In another embodiment of the present invention, the ligand DNA is the BSV env gene, which functions in the context of the invention in a similar manner.

In another preferred embodiment, the present invention exploits the fact that nonmammalian viruses normally do not terminate glycoproteins with sialic acid. Thus, the ligand DNA is a gene which expresses an asialoglycoprotein, which binds to mammalian lectins (e.g., the hepatic asialoglycoprotein receptor), which would then facilitate entry into the mammalian cell.

Replication and Encapsidation Nucleic Acids

The replication and encapsidation functions are required for replication, excision and encapsidation of the recombinant viral genome into an infectious recombinant virion or virus. Each type of recombinant virus will require a different type of replication and encapsidation function. For instance, if the recombinant virus is a retrovirus, then the replication and encapsidation functions include the retroviral gag, pol and env genes (and in the case of lentiviruses will also include regulatory or accessory genes such as HIV tat, rev, nef, vpu or vpr), while if the recombinant virus is an AAV, then the replication and encapsidation functions include the rep and cap genes from an AAV.

As discussed above, either the carrier vector or the mammalian host cell may comprise nucleic acids encoding those replication and encapsidation functions required for a particular recombinant virus. Mammalian host cells such as A64 cell line described in U.S. Pat. No. 5,658,785 and the B50 cell line described in PCT US98/19463) express AAV rep and cap genes for replication and packaging of recombinant AAV. Similarly, mammalian host cells expressing adenoviral genes required for replication and packaging of recombinant adenovirus are known [see, e.g., U.S. Pat. No. 5,851,806 and Amaltifano et al., *Proc. Natl. Acad. Sci.* USA 93:3352–6 (1996)] or may be constructed, and a number of mammalian host cells expressing retroviral genes required for replication and packaging of recombinant retroviruses have been constructed [see, e.g., Cone et al., Proc. Natl. Acad. Sci. USA 81:6349–6353 (1984); Miller et al., Mol. Cell. Biol. 6:2895–2902 (1986); Miller et al., Mol. Cell. Biol. 5:431–437 (1985); and Sorge et al., Mol. Cell. Biol. 4:1730–1737 (1984)]. Cell lines comprising genes required for packaging of herpesviruses (see, e.g., U.S. Pat. No. 5,851,826) are also known.

If a cell line comprises all the necessary replication and encapsidation functions to replicate, excise and package a particular recombinant viral genome, then the carrier vector need not comprise any replication and/or encapsidation nucleic acid sequences. The cell line may comprise the necessary replication and encapsidation functions either by being transiently or stably transduced with the nucleic acid encoding the appropriate proteins. In a preferred embodiment, the cell line stably comprises the replication and encapsidation functions. Furthermore, the cell line may express the replication and encapsidation functions constitutively or inducibly. Constitutive or inducible expression may be controlled by using any of the expression regulatory sequences known in the art or as discussed above under "Expression Regulatory Sequences." In a preferred embodiment, the expression of the replication and encapsidation functions is inducible. In a more preferred embodiment, the replication and encapsidation functions are stably transfected or infected and are inducibly expressed. In an even more preferred embodiment, the expression of the replication and encapsidation functions is regulated by their native promoters.

A mammalian cell line used in the instant invention may comprise none of the functions required for replication or encapsidation, or may comprise only a part of the functions required for replication or encapsidation. If a mammalian cell line comprises none of the functions required for replication or encapsidation, these functions must be introduced into the cell by a vector for production of the recombinant virus. In a preferred embodiment, one or more carrier viruses of the instant invention are used to transduce the mammalian cell line with the nucleic acids encoding the replication and encapsidation functions. In a more preferred embodiment, a single carrier virus comprising the replication and encapsidation functions are used to transduce the mammalian cell line. In an even more preferred embodiment, a single carrier virus comprising the replication and encapsidation functions, the embedded recombinant viral genome, and any other nucleic acid sequences required for recombinant virus production are used to transduce the mammalian cell line.

If the mammalian cell line comprises some of the replication or encapsidation functions, these functions must be introduced into the cell by a vector for production of the recombinant virus. In a preferred embodiment, one or more carrier viruses are used to transduce the mammalian cell line with the nucleic acids encoding the missing replication and encapsidation functions. In a more preferred embodiment, a single carrier virus comprising the missing replication and encapsidation functions are used to transduce the mammalian cell line. In an even more preferred embodiment, a single carrier virus comprising the missing replication and encapsidation functions, the embedded recombinant viral genome, and any other nucleic acid sequences required for recombinant virus production are used to transduce the mammalian cell line.

The replication and encapsidation functions required for a recombinant virus differ depending upon the type of recombinant virus. In general, the required replication and encapsidation functions are known in the art for the various recombinant viruses. In preferred embodiment of recombinant vectors, recombinant AAV requires rep and cap for replication and encapsidation, recombinant retroviruses require gag, pol and env (and tat, rev and nef for lentiviruses), recombinant adenoviruses require all of part of the functions encoded by E1, E2, E4, L1-L5, pIX and IVa2 genes, alone or in combination, and recombinant herpesviruses require a large number of genes, which may be provided by a helper herpesvirus or by a carrier vector comprising the required herpesvirus genes. Together the host mammalian cell and the carrier virus must contribute the necessary replication and encapsidation functions for the particular recombinant virus in order to obtain infectious recombinant virus from the mammalian host cells.

In one embodiment, the replication and encapsidation functions are encoded by nucleic acids encoding the naturally-occurring proteins having the replication and encapsidation functions. In another embodiment, the replication and encapsidation functions are encoded by nucleic acids encoding fragments or muteins of the naturally-occurring proteins but which retain their respective replication and encapsidation functions. In another embodiment of the invention, other recombinant viruses may be produced using nucleic acids encoding the appropriate replication and encapsidation functions for the particular recombinant virus desired. Other types of recombinant viruses and the replication and encapsidation functions they require are known in the art.

In a preferred embodiment, when production of a recombinant AAV is desired, the rep and cap sequences are regulated by a native AAV p5 promoter. In another preferred embodiment, when production of a recombinant adenovirus is desired, the nucleic acid sequences encoding the replication and encapsidation functions for adenovirus are regulated by their native adenovirus promoters. Native promoters may also be used for regulating the expression of replication and encapsidation functions of other recombinant viruses, including, without limitation, herpesvirus and HBV.

In a more preferred embodiment, the replication and encapsidation functions are encoded by nucleic acid sequences inserted in the carrier vector. The advantage of having these sequences on the carrier vector is that no cell line has to be constructed before infection by the carrier virus. It is often difficult to create and maintain cell lines expressing replication and encapsidation functions because many of the proteins that provide these functions are toxic to mammalian cells. Thus, another advantage of inserting the replication and encapsidation sequences on the carrier vector is that the replication and encapsidation functions are only expressed in the mammalian cells when the cells are infected with the carrier virus when the production of a recombinant virus is desired. In a more preferred embodiment, the carrier virus has an embedded recombinant viral genome comprising a transgene and the ITRs from AAV and further has rep and cap gene sequences for replication and encapsidation of the embedded recombinant AAV genome. In an even more preferred embodiment, the expression of the rep and cap genes is regulated by their native promoters or rep/cap is separated from the promoter to decrease or eliminate homologous or non-homologous recombination to form wt AAV. Similarly, in a preferred embodiment of carrier viruses that produce recombinant retrovirus, adenovirus, herpesvirus and HBV, the carrier viruses contain nucleic acid sequences that encode replication and encapsidation functions. In a more preferred embodiment, the nucleic acid sequences encoding the replication and encapsidation functions are regulated by their native promoters.

Helper Functions

A number of viruses are unable to replicate, excise and package on their own, and require helper functions to do so. Helper functions may also be required for the production of recombinant viruses which have had a large amount of their genome deleted for insertion of the transgene. The nature of the helper function may differ depending upon the type of recombinant virus and/or the amount of genome that has been deleted. Helper functions include viral proteins, non-viral proteins, as well as physical and/or chemical agents. One may identify which helper functions are required from what is known in the art. For instance, it is known that AAV requires helper functions from adenovirus or herpesvirus or from different chemical or physical agents. Alternatively, one of skill in the art may determine what helper functions are required by producing recombinant viruses using the composition and methods disclosed in the instant specification.

To identify which helper functions are required for high levels of recombinant virus production, one may infect mammalian host cells with the carrier virus in the absence of helper functions and measure the titer of infectious recombinant virus. One may then transduce the mammalian host cells with various nucleic acids encoding potential helper functions. Such helper functions may be any nucleic acid that is known or thought to encode a helper function. In a preferred embodiment, the helper function is one or more viral proteins. In a more preferred embodiment, the helper virus proteins are insufficient to produce a mature helper virus. After transducing the mammalian host cell with the nucleic acid encoding the potential helper function, one may then measure the titer of the recombinant virus.

If the carrier virus comprises a recombinant AAV genome, helper functions are required for production of infectious recombinant AAV. In a preferred embodiment, the helper functions are nucleic acids derived from a virus. In a more preferred embodiment, the helper functions are derived from adenovirus, herpes simplex virus (HSV) HSV-1, HSV-2, cytomegalovirus (CMV) or pseudorabies virus (PRV). In an even more preferred embodiment, the helper functions are at least E1a, E1b and E2a from adenovirus, and may also include E4ORF6 and VAI. In another preferred embodiment, the nucleic acid encodes the helper functions from the helicase-primase complex of HSV (UL5, UL8 and UL52) and the major single-stranded DNA binding protein of HSV (UL29). The helper functions may also include all 7 HSV DNA replication genes (UL5, 8, 52, 29, 30, 9 and 42). Alternatively, helper functions for recombinant AAV may be provided by chemical or physical agents, including ultraviolet light, cycloheximide, hydroxyurea and various carcinogens.

The required helper functions for production of a recombinant virus may be delivered to the mammalian host cell by any method known in art. The helper functions may be delivered by transfection with a vector, such as a plasmid, by infection with a viral vector comprising the helper functions, or by any other method known in the art, including those discussed above (e.g., biolistic injection of DNA, use of DNA conjugates, etc.). The transfection or infection may be stable or transient. Alternatively, the mammalian cell line may stably express (either on an extrachromosomal episome or through integration in the cell's genome) the helper functions. In addition, some of the helper functions may be expressed by the mammalian cell line while other helper functions are introduced by a vector. For example, 293 cells (ATCC CRL-1573) constitutively produce adenoviral E1a and E1b proteins. Thus, for production of recombinant AAV, the helper functions required for the production of infectious recombinant AAV, such as E2A, E4ORF6 and VAI, are introduced into the host cell by transfection or infection of a vector.

In a preferred embodiment, the helper functions are transduced into the mammalian cells by a carrier virus. In a more preferred embodiment, some or all of the helper functions are transduced into the mammalian cell by a carrier virus comprising the embedded recombinant viral genome. In an even more preferred embodiment, all of the helper functions are transduced into the mammalian cell by a carrier virus comprising the embedded recombinant viral genome, any required replication and encapsidation functions, and, optionally, a ligand DNA. In the most preferred embodiment, the carrier vector has a baculovirus backbone. An internal ribosome entry site (IRES) sequence may be placed between E2A and E4orf6 if only a single promoter is to be used for these two proteins. Alternatively, each helper function gene may be supplied with its own promoter. These genes may be under the regulatory control of a variety of promoters, constitutive or inducible, such as the CMV immediate-early promoter/enhancer or the MMTV LTR, respectively. Whether the helper functions are provided on the carrier vector itself or are provided by the host cells, the promoters regulating those genes may be constitutive or inducible.

The expression of the helper functions may be regulated by any of the expression regulatory sequences known in the art or as described above, including cis or trans regulation. The expression regulatory sequences may provide for constitutive expression, inducible expression, tissue-, cell type- or differentiation state-specific expression, or expression from the helper function protein's native promoter. In a preferred embodiment, the native promoter of the helper function protein is used. In another preferred embodiment, an inducible promoter of a helper function protein is used. In another preferred embodiment, a constitutive promoter of a helper function protein is used. In a further preferred embodiment, the constitutive promoter is the CMV promoter. In another preferred embodiment, one or more constitutive promoters are used for certain helper function proteins, and one or more native promoters are used for other helper function proteins.

In one embodiment, each protein or polypeptide required for helper function is encoded by a nucleic acid whose expression is regulated by its own promoter and polyadenylation signal, as well as optional sequences such as enhancers. In another embodiment, a nucleic acid is transcribed to a single transcript that encodes more than one protein or polypeptide required for helper function. In this case, an IRES may be placed between the coding sequences of each of the individual proteins or polypeptide to permit subsequent translation of the polycistronic mRNA. If only a single polycistronic transcript is produced, only a single promoter, optional enhancer, and polyadenylation signal are required for regulation of the transcription of the nucleic acid encoding the helper function. One may also encode the helper function by using both monocistronic mRNAs that encode single proteins and polycistronic mRNAs encoding multiple proteins.

In a preferred embodiment of the instant invention, the carrier vector comprises a embedded recombinant AAV genome and helper functions. In a further preferred embodiment, the helper functions comprise adenovirus E1a, E1b and E2a, and more preferably include E4ORF6 and VAI. In an even more preferred embodiment, the helper functions are encoded by a single polycistronic transcript, and the promoter for the helper functions is a constitutive promoter, preferably the CMV promoter.

Other recombinant viruses would require different helper functions or none at all, but in all cases those helper functions may be provided on the carrier vector that carries the embedded recombinant viral genome, on a separate carrier virus, on a different type of vector capable of transducing a mammalian host cell, or is endogenously expressed in the mammalian host cell itself Mammalian Host Cells Any type of mammalian host cell which can be adapted to cell culture may be used to produce the recombinant viral genome. In general, a mammalian host cell used in this invention is one that may be infected by a nonmammalian carrier virus. The mammalian host cell may be one that may be infected by a nonmammalian carrier virus that does not express a ligand encoded by a ligand nucleic acid, may be one that may be infected by a nonmammalian carrier virus that expresses a ligand encoded by a ligand nucleic acid, or may be a cell that is infected by a carrier vector that either expresses or does not express a ligand nucleic acid. Alternatively, the mammalian host cell may be one that is not usually infected by a carrier virus, but which can be transduced with a cellular receptor such that it may bind to a nonmammalian host cell. For instance, a mammalian host cell may be transduced with a growth factor receptor such that it can be infected by a carrier virus that expresses the particular growth factor as its ligand.

In addition to the ability to be infected by the carrier virus, another preferred characteristic of the mammalian host cell is that it is able to uncoat the nonmammalian carrier virus. A third preferred characteristic of the mammalian host cell is its ability to replicate the recombinant virus at high levels. In a preferred embodiment, the mammalian host cell is one that takes up the nonmammalian carrier virus at high levels, uncoats the carrier virus efficiently, and replicates the recombinant virus at high levels.

Appropriate mammalian host cells include, without limitation, CHO, BHK, MDCK and various murine cells, e.g., 10T1/2 and WEHI cells, African green monkey cells such as COS 1, COS 7, BSC 1, BSC 40, and BMT 10, and human cells such as VERO, WI38, MRC5, A549, and HT1080 cells. In a preferred embodiment, appropriate mammalian cell include 293 cells (human embryonic kidney cells which express adenoviral E1a and E1b proteins), B-50 cells (HeLa cells which express AAV rep and cap, see PCT US98/19463), 3T3 cells (mouse embryonic fibroblast cell line), NIH3T3 cells (subline of 3T3 cells), HepG2 cells (human liver carcinoma cell line), Saos-2 cells (human osteogenic sarcoma cell line), HuH7 cells or HeLa cells (human carcinoma cell line).

In addition to the mammalian host cells listed above, other mammalian host cells may be used. One may determine whether a cell line would be suited for use as a mammalian host cell by infecting the cell line with a carrier virus containing all the required components to produce a recombinant virus, culturing the cells under conditions in which recombinant virus is produced, and then measuring the titer of infectious recombinant virus that is produced. One may then compare the titer of infectious virus produced in the potential host cell with the titers produced by other host cells to determine whether the cell line is good for recombinant virus production.

Although the receptor(s) for nonmammalian carrier virus such as baculovirus on both insect and mammalian cell is/are unknown, it is thought that the baculovirus may bind to the cell, at least in part, via heparan sulfate expressed on the cell surface. Without wishing to be bound by any theory, cells which express high levels of heparan sulfate on their cell surface may be more easily infected by carrier viruses, especially baculovirus, than cells which express low levels of heparan sulfate on their cell surface. Thus, one method of identifying whether a particular cell line is a potential mammalian host cell is to measure the level of heparan sulfate on the cell surface.

Method of Making and Producing Carrier Viruses

The present invention includes methods of constructing the novel carrier vectors described above and producing large quantities of the carrier vector. This method comprises the steps of:

1. Modifying a nonmammalian virus backbone DNA, or a replication-proficient portion thereof, by inserting one or more nucleic acid inserts comprising 1) a recombinant viral genome comprising a transgene operably linked to expression regulatory sequences and flanked by flanking elements; 2) nucleic acid sequences encoding helper functions operably linked to expression regulatory sequences; 3) nucleic acid sequences encoding replication and/or encapsidation functions for the recombinant virus; 4) a ligand DNA operably linked to expression regulatory sequences that are active in nonmammalian cells; and 5) regulatory control sequences that regulate sequences in the nonmammalian virus backbone, a modified nonmammalian virus backbone or a replication-proficient portion of the backbone or modified backbone;
2. transducing the resulting carrier vector into nonmammalian host cells,
3. growing the nonmammalian host cells under conditions in which carrier virus is produced; and
4. collecting the carrier virus from the nonmammalian host cells.

In a preferred embodiment, the carrier vector will be modified such that it comprises the recombinant viral genome. In a more preferred embodiment, the carrier vector will be modified such that it comprises the recombinant viral genome and either or both of the nucleic acid inserts encoding the replication and/or encapsidation functions and the helper functions required for production of a recombinant virus. In an even more preferred embodiment, the carrier vector will be modified such that it comprises the recombinant viral genome, all of the nucleic acid inserts encoding the replication and/or encapsidation functions and the helper functions required for production of a recombinant virus, and the nucleic acid insert encoding the ligand.

The nonmammalian host cell may be any host cell known in the art or described in Table 1 of U.S. Pat. No. 5,731,182. The nonmammalian virus backbone DNA may be derived from any virus that infects nonmammalian species, including those known in the art or described in Table 1 of U.S. Pat. No. 5,731,182. In a preferred embodiment, the nonmammalian backbone of the carrier vector is derived from a baculovirus and the nonmammalian host cells are insect cells. In a more preferred embodiment, the carrier virus produced by the baculoviral carrier virus in the insect cells is produced at a high titer. Preferably, when baculovirus is used, the titers of the carrier baculovirus produced in any embodiment are greater than $10^8$ pfu/ml in insect cells or $10^9$ pfu/ml; more preferably, the titers are greater than $10^{10}$ pfu/ml or $10^{11}$ pfu/ml; and even more preferably, the titers are greater than $10^{12}$ pfu/ml. The instant invention also encompasses lysates and supernatants of nonmammalian host cells comprising baculoviral carrier viruses having similar titers.

The nonmammalian host cells comprising the carrier vector may be grown by any method known in the art or as described herein. Methods for producing large amounts of nonmammalian viruses are well known in the art and are described in U.S. Pat. No. 5,871,986. The nonmammalian carrier virus may be purified from the supernatant produced by the nonmammalian host cells or from lysed cells by any method known in the art or as described herein. Methods for collecting and purifying nonmammalian viruses are well known in the art and are described in U.S. Pat. No. 5,871, 986. A method of collecting and purifying the nonmammalian viruses is described in Example 6.

The carrier virus produced when the carrier vector is encapsidated has the normal wild-type capsid optionally modified by addition of the ligand. In general, the expression of the ligand nucleic acid is regulated by expression regulatory sequences which promote transcription and translation in the nonmammalian host cells. Such expression regulatory sequences may include a nonmammalian promoter active in the nonmammalian host cells of interest, and may optionally include enhancer sequences, polyadenylation signals, or any other expression regulatory sequences known in the art or described above. In a preferred embodiment, the other nucleic acid inserts in the nonmammalian backbone may not be expressed or may be expressed at lower levels because their promoters are inactive or less active in nonmammalian cells. Because potentially toxic viral components, such as helper functions or replication/ encapsidation functions, are either not expressed or expressed at lower levels, a high titer of carrier virus may be produced in nonmammalian cells.

Methods of Producing Recombinant Virus From the Carrier Vector

Another aspect of the instant invention is a method of producing recombinant virus by using a carrier virus, produced by the method described above, to infect mammalian cells and subsequently collecting and purifying the recombinant virus from the mammalian cells. The method comprises the steps of 1. Infecting mammalian host cells with a carrier virus, wherein he carrier virus optionally expresses a ligand on the surface of the carrier virus;
2. growing the infected mammalian host cells under conditions in which the embedded recombinant viral genome is replicated, excised and encapsidated; and
3. collecting the recombinant virus from the mammalian host cells.

The mammalian host cells may be any mammalian host cell known in the art, described in the specification above under "Mammalian Host Cells," or identified by the method described under "Mammalian Host Cells" as an appropriate host cell. The mammalian host cell, prior to infection, may be one that expresses one or more of the following: 1) replication and/or encapsidation functions (e.g., B-50 cells or one of the retroviral cell lines described previously); 2) some or all necessary helper functions (e.g., 293 cells); and/or 3) an embedded recombinant viral genome stably integrated in the mammalian host cell genome. Alternatively, the mammalian host cell comprises none of these other elements before infection by the carrier virus.

The mammalian host cells may be infected and grown by any method known in the art or as described herein. Methods for infecting mammalian host cells with nonmammalian viruses are described herein and in Barsoum et al., supra. Once the mammalian host cell has been infected, the expression regulatory sequences that are operably linked to any required replication and/or encapsidation functions and helper functions are activated. Expression of the replication and/or encapsidation functions and helper functions, along with the mammalian host cell's native transcriptional and translational components, permits replication, excision and encapsidation of the embedded recombinant viral genome, thereby causing the manufacture of the recombinant virus.

In general, the nonmanimalian carrier virus is capable of infecting a mammalian cell, but the carrier virus will not replicate in the mammalian cell because the components required for replication of the nonmammalian carrier virus are not present in the mammalian cell. If the carrier virus comprises a ligand nucleic acid the expression regulatory sequences controlling ligand expression generally will not function in mammalian cells, such that ligand expression does not occur in the mammalian host cell. However, if replication of the carrier virus or if expression of the ligand is desired in the mammalian host cell, then additional expression regulatory sequences may be operably linked to the sequences required for replication, excision and/or packaging of the nonmammalian carrier virus and/or expression of the ligand.

The recombinant virus may be purified from the supernatant produced by the mammalian host cells or from lysed cells by any method known in the art or as described herein. Methods for collecting and purifying various types of recombinant viruses from mammalian host cells are well known in the art and are described in PCT US97/15716. A method of collecting and purifying the recombinant viruses is also described in Example 6.

As discussed above, in a preferred embodiment, one or more carrier viruses comprises all those nucleic acid inserts required for production of recombinant virus in a particular mammalian host cell. Thus, if the host cell comprises replication and encapsidation functions, then the carrier viruses comprise the embedded recombinant viral genome and any necessary helper functions. Similarly, if the host cell comprises the embedded recombinant viral genome, then one or more carrier viruses will comprise the required replication and encapsidation functions and any necessary helper functions, while if the host cell comprises the necessary helper functions, then one or more carrier viruses will comprise the required replication and encapsidation functions and the embedded recombinant viral genome.

In a preferred embodiment, a single carrier virus comprises all of the nucleic acid inserts required for production of a recombinant virus in a particular mammalian host cell. For example, if a recombinant AAV is to be produced in B-50 cells, the carrier virus will comprise the embedded recombinant viral genome and those helper functions required for AAV production. Similarly, if a recombinant AAV is to be produced in a mammalian host cell that does not express any of the required functions for AAV production, the carrier virus will comprise the embedded recombinant viral genome, the replication and encapsidation functions and the helper functions required for AAV production.

The method of producing recombinant virus described is useful because it produces an essentially homogeneous recombinant virus that is free from helper virus and wild-type virus without purification. The recombinant virus is free from helper virus because there are insufficient helper virus genes to produce a mature helper virus. The recombinant virus is free of wild-type virus because homologous recombination is avoided by a variety of techniques. For instance, wild-type AAV produced through homologous recombination may be avoided using several strategies. The rep/cap sequences and the embedded recombinant viral genome may be positioned at separate loci on the carrier vector, minimizing the likelihood of a recombination event. The rep/cap sequences and the embedded recombinant viral genome also may be designed so that they have no regions of homology. Additionally, because AAV is intolerant of packaging greater than 5.0 kb, one may incorporate a "stuffer" nucleic acid sequence to be inserted between a required sequence, such as rep or cap and its promoter. Thus, even if recombination took place, the resulting AAV genome would be too large to package and no wtAAV would be produced. In order to maintain the integrity of translation of rep, the stuffer sequence may be constructed using splice donor and acceptor sites, such that the resulting mRNA and ultimately the rep protein produced would be unaffected. Similar methods may be employed for other types of recombinant viruses to avoid recombination and production of wild-type virus.

The method is also easily scaled to industrial production because it may require only a single infection of mammalian host cells by a carrier virus that can be produced in large amounts at high titers. In a preferred embodiment, the recombinant virus produced by the instantly described method is produced at a high titer. For recombinant AAV, the titer is preferably greater than $10^4$ particles per producing cell, more preferably, greater than $10^5$ to $10^6$ particles per producing cell, and even more preferably, greater than $10^7$ particles per producing cell. For recombinant adenovirus, the titer is preferably greater than $10^4$ particles per producing cell, more preferably, greater than $10^5$ particles per producing cell, and even more preferably, greater than $10^6$ particles per producing cell. For recombinant herpesvirus, the titer preferably is greater than $10^{10}$ pfu per ml, more preferably, greater than $10^{11}$ pfu per ml and even more preferably, greater than $10^{13}$ pfu per ml, For retroviruses, the titer preferably is greater than $10^6$ to $10^7$ colony forming units (cfu) per ml, more preferably, $10^8$ cfu per ml, and even more preferably, $10^9$ cfu per ml. The instant invention also encompasses lysates and supernatants of mammalian host cells comprising recombinant viruses. These lysates and supernatants differ from those produced by prior art methods because they do not contain wild-type virus or helper virus.

In a preferred embodiment, the method is used to manufacture recombinant AAV at high titers and in the absence of helper virus or wild-type AAV. The desired transgene, with appropriate expression regulatory sequences operably linked thereto, is placed between the AAV ITRs, by means known in the art. In order to maintain the length of the insert at a length compatible with eventual packaging, spacer DNA may optionally be inserted therein. This recombinant viral genome is then embedded in a baculovirus, in a non-essential locus, by means known in the art. The required helper functions, replication and encapsidation functions, and/or embedded recombinant viral genome may be placed in the polyhedrin gene site, the p10 gene site, or one could be placed at the polyhedrin gene site and the other may be placed at the p10 gene site (see FIG. 1). The baculovirus backbone also may be modified to comprise a ligand nucleic acid, such as the VSV-G gene. The baculovirus may also be modified to comprise rep and cap sequences and helper functions from adenovirus, comprising E1a, E1b, E2a. E4ORF6 and VAI, or HSV genes UL5, UL8, UL52 and UL29. The carrier vector is transduced into insect cells, such as Sf9 cells, the cells are grown under conditions in which baculovirus is produced, and the baculovirus is collected and purified. The baculovirus is then used to infect mammalian cells, the mammalian cells are grown under conditions in which the recombinant virus is replicated, excised and encapsidated, and the recombinant AAV is collected and, optionally, purified.

In another preferred embodiment, the method is used to manufacture recombinant "gutless" adenovirus deleted of all adenoviral genes at high titers and in the absence of helper virus or wild-type adenovirus. Previously, one would make a "gutted" adenovirus plasmid from the adenovirus genome in which all of the adenovirus genes were removed except for the ITRs and the cis-acting packaging signal. Foreign DNA containing the transgene of interest, transcriptional regulatory sequences, and, optionally, stuffer DNA would be added to obtain an insert of approximately 36 kb. The plasmid is designed such that a DNA cassette contains the packaging signal upstream of the transgene and stuffer DNA, and the Ad ITRs flank such DNA cassette. The plasmid was transfected into cells, such as 293 cells. A helper adenovirus lacking the adenoviral E1 and E3 genes, as well as sequences within the adenoviral packaging signal was used to infect the 293 cells transfected with the gutted Ad plasmid to provide replication and encapsidation functions in trans. Using this method, low levels of homologous recombination would rescue the deletion in the helper Ad's packaging signal, thus both helper and "gutless" adenovirus would be produced. CsCl gradients would have to be performed to separate the helper adenovirus from the recombinant "gutless" adenovirus vector. In addition, other disadvantages included high levels of contaminating helper virus and low yields of the gutless Ad vector.

Using the method of the instant invention, homologous recombination resulting in generation of contaminating helper Ad can be avoided. Rather than using helper adenovirus, one may construct a carrier vector comprising the adenoviral functions necessary for replication and packaging of the gutted Ad genome. In one embodiment, the carrier vector contains the complete genome of adenovirus without the ITR's, E1, the packaging signal, and, optionally, without E3. Then, one may infect mammalian cells with the carrier virus and transfect the cells with the plasmid described above containing the transgene, ITRs and packaging signal. In another embodiment, one may construct two separate carrier vectors, one comprising helper adenoviral functions described above and the other comprising the gutted Ad construct containing the Ad ITR's, packaging signal and the transgene cassette. Alternatively, one may construct a single carrier vector comprising both the helper adenoviral functions and the transgene cassette comprising the ITRs, packaging signal and transgene/stuffer DNA. The adenoviral functions and transgene cassette may be placed in the polyhedrin gene locus, the p10 gene locus, or one could be placed at the polyhedrin gene locus and the other may be placed at the p10 gene locus (see FIG. 1).

In another preferred embodiment, the method is used to manufacture recombinant herpesvirus amplicon vectors. As discussed above, herpesvirus amplicons require the "a" sequence for packaging, and the HSV origin of replication. Either the $ori_S$ or $ori_L$ origin of replication may be used, but the oris origin is preferred. One may construct a carrier vector comprising a herpesvirus amplicon. In one embodiment, the cassette would contain, in the 5' to 3' direction, the "a" sequence, followed by the transgene of interest, followed by the HSV origin of replication, followed by an optional spacer, and followed by another "a" sequence. This may be inserted into either the polyhedrin or the p10 gene loci in baculovirus, for instance. The carrier virus that is subsequently produced may be used to infect mammalian cells that have been coinfected with helper herpesvirus. Alternatively, the helper herpesvirus functions may be placed on the same or a separate carrier vector and used to infect the mammalian cells. Recombinant herpesvirus amplicon vectors may then be isolated and purified from the mammalian cells.

Recombinant Virus Compositions

Another embodiment of the present invention is the recombinant virus produced by the methods of the invention. Unlike other preparations of recombinant virus, the preparations produced by the methods of this invention yield high titers of essentially homogeneous recombinant virus which is helper-free and wild-type virus free. The recombinant virus may be formulated as a pharmacological composition for use for any form of transient and stable gene transfer in vivo and in vitro. The recombinant virus may be used for in vivo and ex vivo gene therapy, genetic immunization, in vitro protein production and diagnostic assays.

For gene therapy, the recombinant virus may be introduced into cells ex vivo or in vivo. Where the virus is introduced into a cell ex vivo, the recombinant virus may be used to infect a cell in vitro, and then the cell may subsequently be introduced into a mammal (e.g., into the portal vein or into the spleen), if desired. Alternatively, the recombinant virus may be administered to a mammal directly, e.g., intravenously or intraperitoneally. A slow-release device, such as an implantable pump, may be used to facilitate delivery of the virus to a cell. Where the virus is administered to a mammnal, the specific cells to be infected may be targeted by controlling the method of delivery. For example, intravascular administration of the recombinant virus to the portal vein or to the hepatic artery may be used to facilitate targeting the recombinant virus to a liver cell.

The recombinant virus produced by the above-described method may be administered to a patient, preferably suspended in a biologically compatible solution or pharmaceutically acceptable delivery vehicle. A suitable vehicle includes sterile saline. Other aqueous and non-aqueous sterile suspensions known to be pharmaceutically acceptable carrier and well known to those of skill in the art may be employed for this purpose.

The recombinant virus is administered in sufficient amounts to infect the desired cells and provide sufficient levels of transduction and expression of the selected transgene (or viral gene products in the case of a vaccine) to provide a corrective effect without undue adverse or with medically acceptable physiological effects, which can be determined by those skilled in the medical arts. Conventional and pharmaceutically acceptable routes of administration include direct administration to the target organ, tissue or site; intranasal; intravenous; intramuscular; subcutaneous; intradermal; oral and other parenteral routes of administration. Routes of administration may be combined, if desired.

Dosages of the recombinant virus will depend primarily on factors such as the type of recombinant virus (i.e., whether the virus is AAV, adenovirus, retrovirus, etc.), the condition being treated and the selected gene. The dosage may also vary depending upon the age, weight and health of the patient. For example, an effective human dosage of a recombinant adenovirus is generally in the range of from about 0.5 ml to 50 ml of saline solution containing adenovirus at concentrations of $1 \times 10^7$ or $1 \times 10^8$ or $1 \times 10^9$ or $1 \times 10^{10}$ or $1 \times 10^{11}$ or $1 \times 10^{12}$ or $1 \times 10^{13}$ or $1 \times 10^{14}$ or $1 \times 10^{15}$ particles per dose administered. The dosage will be adjusted to balance the corrective benefits against any adverse side effects. The levels of expression of the selected gene may be monitored to determine the type and frequency of dosage administration.

The following examples of the present inventions are illustrative only, and are not intended to limit the scope of the invention.

EXAMPLE 1

Cell Line Maintenance and Virus Propagation

The human embryonic kidney cell line 293 (ATCC CRL 1573) was maintained in Dulbecco's Modification of Eagle's Medium (DMEM, GIBCO BRL) supplemented with 10% FBS (Hyclone) and 50 µg of penicillin, 50 µg of streptomycin, and 10 µg of neomycin/ml (GIBCO BRL). Insect cell line IPLB-Sf21 (CLONTECH Laboratories, Inc.) was maintained in SF900-II medium (GIBCO BRL) supplemented with 10% FBS and 50 µg of penicillin, 50 µg of streptomycin, and 10 µg of neomycin/ml. Human adenovirus type 5 (ATCC VR-5) was propagated on 293 cells and purified through CsCl gradient centrifugation (Jones and Shenk, 1978).

EXAMPLE 2

Recombinant Plasmid Construction

Standard DNA recombinant techniques were employed to create recombinant plasmids (Sambrook et al, 1989). The Rep and Cap sequence of pAV2 (ATCC 37216) between the DraIII site upstream of the p5 promoter and the NcoI site downstream of the polyadenylation signal was removed. The Rep and Cap sequence was replaced through multiple cloning steps with a cassette containing GFP under the control of elongation factor 1 alpha (EF1α) promoter to create pAV2cisEFGFP (FIG. 2). The entire cassette containing both AAV ITRs and the GFP gene was then cloned into the SpeI and BglII sites of BV-CZPG (baculovirus shuttle plasmid with VSV-G gene under control of polyhedrin promoter; kindly provided by Dr. Jim Barsoum of Biogen, Inc.) through multiple cloning steps to obtain pBV-cisEFGFP (FIG. 3).

Adenovirus helper genes E2A, E4ORF6, and VAI were subcloned from Ad5 DNA. Briefly, E4ORF6 was first inserted into the SmaI and XbaI sites of pIRES1neo (CLONTECH Laboratories, Inc.) to obtain pIRESORF6. Next, a Sau3AI-BsrGI fragment containing E2A coding sequences was inserted into the BamHI/BstXI sites of the plasmid pIRESORF6 through multiple cloning steps to obtain the plasmid pE2AiORF6. In this construct, E2A and E4ORF6 genes are separated by an encephalomyocarditis virus (ECMV)-derived IRES, and both genes are under the transcriptional control of a single human cytomegalovirus (CMV) promoter upstream of the E2A gene. Next, a NcoI-BamHI fragment of Ad5 DNA containing the VAI gene was inserted into the XhoI site of pE2AiORF6 through blunt-end cloning to obtain pE2AiORF6-VAI. The entire cassette containing CMV-E2AiORF6-VAI was cloned into the HpaI and SpeI sites of the baculovirus shuttle plasmid BV-CZPG to obtain pBV-EiOV (FIG. 2).

AAV-2 rep and cap genes located between a Dra III site, which is upstream of the AAV-2 p5 promoter and a BsaI site, which is downstream of the polyadenylation signal (FIG. 2), were cloned into the SpeI and PacI sites of pBV-EiOV through multiple cloning steps to obtain pBV-EiOV-RC (FIG. 3). Ad5 E1 and cisEFGFP were cloned into pBV-EiOV through multiple steps to obtain the pBV-EiOV-cisEFGFP-E1 plasmid (FIG. 3). Plasmid pAc-cisEFGFP was constructed by inserting a cassette containing the GFP gene flanked by AAV-2 ITRs into pAcUW1 (Pharmingen) through several cloning steps. The XbaI-SspI fragment of EBVOri from pEBVHisA (Invitrogen) was inserted into pBV-cisEFGFP and pBV-EiOV-RC to create pBV-cisEFGFP-EBVOri (FIG. 3) and pBV-EiOV-RC-EBVOri (FIG. 3). AAV-2 rep and cap genes were cloned into pAdΔF6 (plasmid carrying Ad helper genes E2A, the entire E4, and VAI, kindly provided by Dr. Guangping Gao of the University of Pennsylvania) to obtain pAdΔF6-RC (FIG. 3).

Reference to a construct preceded by a "p" refers to a plasmid, while reference to a construct without a "p" preceding it refers to a virus. For example, pBV-EiOV-RC refers to a plasmid, while BV-EiOV-RC refers to a modified baculovirus.

EXAMPLE 3

Transfection of 293 Cells and Selection for 293-CG3 Stable Cell Line 293 cells were grown to ~70% confluency in 6-cm dia. tissue culture dishes and co-transfected overnight with 1 μg pIRES1neo and 10 μg pAV2cisEFGFP by the calcium phosphate transfection method (Sambrook et al., 1989). Cells were fed with fresh medium containing 10% FBS and cultured for 24 hours. Following trypsinization, cells were seeded at a 1:20 dilution in fresh medium containing 10% FBS. After incubation for another 24 hours, fresh medium containing 1,250 μg/ml of G418 (GIBCO BRL) was added to the cell monolayer to select for G418-resistant cells. The medium containing G418 was replaced every 3–4 days until most of the original G418-resistant cell colonies had formed. A total of fifty colonies were picked, six of which demonstrated constitutive GFP expression. These six clones were expanded in the presence of G418 and tested for their ability to rescue functional rAAV by transfection with plasmid pBV-EiOV-RC. Normally, when a clone was established, it was maintained in G418-containing medium for 3 to 5 passages to ensure that all nonresistant cells had been killed. Then, the cells were maintained in G418-free medium. One cell clone, 293-CG3, showed high efficiency of rAAV rescue and was expanded and used for further experiments.

EXAMPLE 4

Functional Test of 293-CG3 for rAAV Production

Several plasmids were used to test the efficiency of 293-CG3 cells for rAAV production. The cells were first seeded on 6-well plates at a density of 1×10$^6$ cells/well at 2 to 4 hours before transfection. The cells in each well received 5 μg of plasmid DNA in a final volume of 167 μl of CaPO$_4$ (Sambrook et al., 1989). After incubation for 16 hours, cells were fed with fresh medium. Three days later, cells were harvested and rAAV titers (transducing units) were determined. The results are presented in Table 1 as an average of values determined from two separate experiments. They indicate that the 293-CG3 cell line is very efficient for rAAV production, producing approximately 30 to 170 transducing units of rAAV per cell depending on the configuration of helper plasmid used.

TABLE 1

| Transfection | Plasmid (5 μg) | Cell line | rAAV titer (TU/10$^6$ cells) |
|---|---|---|---|
| 1. | pBV-EiOV-RC | 293-CG3 | 3.1 × 10$^7$ |
| 2. | pAdΔF6-RC | 293-CG3 | 1.7 × 10$^8$ |
| 3. | pBV-EiOV | 293-CG3 | 0 |
| 4. | pBV-RC | 293-CG3 | 0 |

EXAMPLE 5

Generation of Recombinant Baculoviruses

To create VSV-G pseudotyped recombinant baculoviruses, the BacPAK baculovirus expression system (CLONTECH Laboratories, Inc.) was used. Plasmid DNA, one of pBV-EiOV-RC, pBV-cisEFGFP, or pBV-EiOV-cisEFGFP-E1, was cotransfected with Bsu36I-digested BacPAK6 DNA into Sf21 cells according to the manufacturer's protocol. The medium was harvested 3 days after transfection and recombinant baculoviruses were screened on 96-well plates by limited dilution assay. Briefly, the medium harvested from transfection was diluted to 10$^{-2}$, 10$^{-3}$, 10$^{-4}$, and 10$^{-5}$ each in 10 ml of insect medium containing Sf21 cells at 2×10$^{-5}$ cells/ml. The mixture was then plated on 96-well plates at 100 μl/well.

After infection for 5–7 days, cells were examined for signs of viral infection (cell fusion mediated by VSV-G expression; see Eidelman et al., 1984). The weels that showed viral infection in the lowest dilution were marked and the virus harvested (Chen et al., 1994). The cells were lysed and used for DNA hybridization to verify the presence of recombinant DNA. Positive clones were amplified into 10 ml, and 1 ml of each clone was used to transduce 293 cells grown in 6-well plates. The 293 cells were transfected with a plasmid carrying the elements not provided by the recombinant baculovirus for rAAV rescue. After transduction for 3 days, cells were lysed and the lysates were used to transduce 84–31 cells (E1/E4 double complementing cell lines derived from 293 cells; see Fischer et al., *J. Virol.*, 70:8934–8943, 1996). The expression of a marker gene indicated the rescuing of rAAV. The cloned that could best support rAAV rescue was screened for 3 to 4 more rounds in order to obtain pure recombinant baculovirus and tested for their support of rAAV rescue Functional clones were further screened on 96-well plates for 3 to 4 rounds to obtain pure recombinant baculoviruses.

To create non-VSV-G pseudotyped recombinant baculoviruses, a Baculovirus Expression Vector System (Pharmingen) was used. Plasmid DNA was co-transfected with baculoviral DNA into Sf21 cells according to manufacturer's protocol. Recombinant baculovirus was screened on 96-well plates the same as described for the VSV-G pseudotyped baculoviruses above except that X-gal staining was used to distinguish recombinant baculovirus from wild type baculovirus.

EXAMPLE 6

Production of rAAV by Using the Methods of This Invention

Method to Transduce Cells

For transduction, recombinant baculoviruses were first pelleted by centrifugation at 4° C. at 20,000 rpm for 30 minutes. The pellets were then resuspended in serum-free DMEM. The medium was removed from the cell monolayer and baculovirus was added to the cells. After incubating for 8–16 hours, cells were fed with fresh medium containing 10% FBS. Cells were harvested 72 hours after transduction. Baculovirus-transduced cells were harvested and lysed in DOC lysis buffer (50 mM Tris-HCl, pH 7.4, 1 mM $MgCl_2$, 0.5% sodium deoxycholate) by sonication on ice water (three sonication pulses for 1 minute each). Cell debris was removed by centrifugation at 13,000 rpm for 5 minutes at 4° C. and the supernatant was collected. The supernatant was used for rAAV titration as described in Example 7.

Transduction of 293 Cells by Baculoviruses BV-EiOV-RC and BV-cisEFGFP

BV-EiOV-RC provides Ad helper genes E2A, E4ORF6, and VAI as well as AAV rep and cap genes. BV-cisEFGFP provides the AAV vector sequence with both AAV ITRs flanking the marker gene GFP. 293 cells express E1a and E1b. Thus, transduction of 293 cells with both BV-EiOV-RC and BV-cisEFGFP provides to the cells the embedded AAV viral genome comprising the GFP transgene operably linked to the EF1α a promoter and flanked by the AAV ITRs; a VSV-G ligand; helper functions comprising E1a, E1b, E2a, E4ORF6, and VAI; and the replication and encapsidation functions, rep and cap. These functions allow the cells to produce recombinant AAV.

Transduction of 293-CG3 Cells by Baculovirus BV-EiOV-RC

Because the AAV vector was stably integrated in the 293-CG3 cells, only BV-EiOV-RC was needed to provide a ligand nucleic acid, helper functions and replication and encapsidation functions to produce recombinant AAV.

Transduction of Rep-Cap Expressing Cells by Baculovirus BV-EiOV-cisEFGFP-E1

The baculovirus BV-EiOV-cisEFGFP-E1 provides the Ad helper genes E1, E2A, E4ORF6, and VAI, as well as the AAV vector with both AAV-ITRS flanking the marker gene GFP. The AAV rep-cap genes are provided by stable rep-cap cell lines such as B50 (Gao et al. 1998).

EXAMPLE 7

Titration of rAAV Produced by Baculovirus Transduction

An rAAV lysate from baculovirus-transduced cells prepared as described in Example 6, was diluted at $10^{-2}$, $10^{-3}$ and $10^{-4}$ with DMEM containing 10% FBS and used for the titration assay. 24-well plates were first coated with 0.1% gelatin for 30 minutes and then plated with $2 \times 10^5$ cells/well of 293-based 84–31 cells (Fischer, et al., 1996). After 3 to 4 hours of incubation, the cells were infected with adenovirus at 100 particles/cell for 30 minutes (adenovirus helps the conversion of single stranded AAV into double stranded AAV and is widely used for AAV titration), and then the diluted rAAV lysate was added. After transduction by the rAAV for 24 hours, the cells were fixed with 4% paraformaldehyde in PBS for 30 minutes. The paraformaldehyde was replaced with PBS, and GFP-expressing cells were counted under by fluorescent microscopy.

EXAMPLE 8

Production of rAAV Using VSV-G Pseudotyped Baculovirus

Recombinant baculovirus BV-EiOV-RC was used to transduce 293-CG3 cells for rAAV production. The cells were first plated on 6-well plates at a density of $1 \times 10^6$ cells/well at 2 to 4 hours prior to transduction. Baculovirus BV-EiOV-RC was concentrated by centrifugation at 20,000 rpm at 4° C. for 30 minutes, resuspended in serum-containing DMEM, and then added to the cells at the indicated amounts as shown in Table 2. After incubation for 16 hours, cells were fed with fresh medium. Following transduction for a total of 3 days, cells were harvested and rAAV titers (transducing units) determined. The results are presented in Table 2 as an average of values determined from two separate experiments. They results indicate that recombinant baculovirus carrying Ad helper and AAV rep-cap genes can successfully transduce 293-CG3 cells and produce rAAV. By increasing the multiplicity of infection (moi) of input baculovirus, higher titers of rAAV were produced.

TABLE 2

| Transduction | BV-EiOV-RC-H6 (pfu/cell) | Cell line | rAAV titers (TU/$10^6$ cells) |
| --- | --- | --- | --- |
| 1. | 0 | 293-CG3 | 0 |
| 2. | 6.25 | 293-CG3 | $1 \times 10^2$ |
| 3. | 12.5 | 293-CG3 | $4.9 \times 10^3$ |
| 4. | 25 | 293-CG3 | $2.6 \times 10^4$ |
| 5. | 50 | 293-CG3 | $2.7 \times 10^5$ |
| 6. | 100 | 293-CG3 | $1.8 \times 10^6$ |

EXAMPLE 9

Transduction Efficiency of Different Mammalian Cell Lines by VSV-G Pseudotyped and Non-Pseudotyped Baculoviruses In order to identify a suitable cell line that is efficiently transduced by baculovirus, a number of cell lines were tested. Cells were seeded on 6-well plates and grown to ~80% confluency. Baculoviruses were added to the cells at the indicated moi's in serum-free DMEM, incubated with the cells overnight, and replaced with fresh medium 12–15 hours later. GFP-expressing cells were scored as a percentage of all cells in the monolayer at 48 hours post-transduction by the recombinant baculovirus.

The results presented in Table 3 indicate that, in general, VSV-G pseudotyped baculovirus (BV-cisEFGFP) transduce mammalian cells much more efficiently than the non-pseudotyped baculovirus (Ac-cisEFGFP). However, HepG2 and Saos-2 cell lines were found to be more transducible than HeLa and 293 cell lines by baculovirus. Insertion of Ad E1 genes into the chromosome of these cell, similar to the scenario in 293 cells, should further facilitate production of rAAV from these cells using the recombinant baculoviruses cited in previous examples. It is noteworthy that Saos-2 cells are highly permissive for infection by baculovirus irrespective of the presence or absence of the VSV-G glycoprotein on the baculoviral coat. The use of this cell line could provide an advantage for rAAV production using non-pseudotyped baculovirus.

All documents cited above are incorporated by reference herein. Numerous modifications and variations of the present invention are included in the above-identified specification and are expected to be obvious to one of skill in the art. Such modifications and alterations to the processes of the present invention are believed to be encompassed in the scope of the claims appended hereto.

TABLE 3

| Trans-duction | Cell line | Baculovirus BV-cisEFGFP | Baculovirus Ac-cisEFGFP | Results % green cells |
|---|---|---|---|---|
| 1. | HepG2 | 10 pfu/cell | | 60 |
| 2. | HepG2 | 50 pfu/cell | | 90 |
| 3. | HepG2 | 100 pfu/cell | | 90 |
| 4. | HepG2 | | 10 pfu/cell | 10~20 |
| 5. | HepG2 | | 50 pfu/cell | 60 |
| 6. | HepG2 | | 100 pfu/cell | 70 |
| 7. | Saos-2 | 10 pfu/cell | | 70 |
| 8. | Saos-2 | 50 pfu/cell | | 100 |
| 9. | Saos-2 | 100 pfu/cell | | 100 |
| 10. | Saos-2 | | 10 pfu/cell | 70 |
| 11. | Saos-2 | | 50 pfu/cell | 100 |
| 12. | Saos-2 | | 100 pfu/cell | 100 |
| 13. | Hela | 10 pfu/cell | | ~5 |
| 14. | Hela | 50 pfu/cell | | ~15 |
| 15. | Hela | 100 pfu/cell | | ~15 |
| 16. | Hela | | 10 pfu/cell | – |
| 17. | Hela | | 50 pfu/cell | – |
| 18. | Hela | | 100 pfu/cell | ~5 |
| 19. | 293 | 10 pfu/cell | | 10 |
| 20. | 293 | 50 pfu/cell | | 50 |
| 21. | 293 | 100 pfu/cell | | 50 |
| 22. | 293 | | 10 pfu/cell | ~5 |
| 23. | 293 | | 50 pfu/cell | 20 |
| 24. | 293 | | 100 pfu/cell | 20 |

References

1. Jones N, Shenk T. Isolation of deletion and substitution mutants of adenovirus type 5. Cell 1978 Jan;13(1):181–8
2. Sambrook, J., Fritsch, E. F., and Maniatis, T. "Molecular Cloning—A Laboratory Manual". Cold Spring Harbor Laboratory Press. 1989.
3. Gao G P, Qu G, Faust L Z, Engdahl R K, Xiao W, Hughes J V, Zoltick P W, Wilson J M. High-titer adeno-associated viral vectors from a Rep/Cap cell line and hybrid shuttle virus. Hum Gene Ther 1998 Nov 1;9(16):2353–62.
4. Fisher K J, Gao G P, Weitzman M D, DeMatteo R, Burda J F, Wilson J M. Transduction with recombinant adeno-associated virus for gene therapy is limited by leading-strand synthesis. J Virol 1996 Jan;70(1):520–32.
5. Eidelman, O., Schlegel, R., Tralka, T. S., and Blumenthal, R. J. Biol. Chem. 1996, 259:4622–4628.
6. Chen, H. and Padmanabhan, R. Biotechniques 1994, 17:40–42.

What is claimed is:

1. A method for producing a recombinant adeno-associated virus (AAV), comprising the steps of:
   a) infecting a mammalian host cell with a carrier virus, wherein said host cell comprises nucleic acid encoding proteins required for replication and encapsidation of the AAV stably integrated in its genome, wherein the carrier virus comprises
      i. a non-mammalian virus nucleic acid backbone that comprises a recombinant AAV genome comprising AAV ITRs and a transgene,
      ii. nucleic acid encoding adenovirus helper function; and
      iii. optionally comprises nucleic acid encoding a ligand expressed on the surface of the non-mammalian virus wherein the ligand binds a mammalian host cell; and
   b) growing the infected mammalian host cell under conditions in which the recombinant AAV genome is replicated, excised and encapsidated.

2. The method according to claim 1, wherein the mammalian host cell is selected from the group consisting of CHO, BHK, MDCK, 10T1/2, WEHI cells, COS, BSC 1, BSC 40, BMT 10, VERO, WI38, MRC5, A549, HT1080, 293, B-50, 3T3, NIH3T3, HepG2, Saos-2, Huh7 and HeLa cells.

3. The method of claim 1, wherein the mammalian host cell is a B-50 cell.

4. The method of claim 1 further comprising the step of collecting the recombinant AAV produced by the mammalian host cells.

5. The method of claim 1 wherein the non-mammalian virus is baculovirus.

6. The method of claim 1 wherein said adenovirus helper function is at least one function selected from the group consisting of adenovirus E1 function, E2a function, E4ORF6 function and VAI.

7. The method of claim 1 wherein said adenovirus helper function is E1 and E2a function.

8. A method for producing a recombinant adeno-associated virus (AAV), comprising the step of growing a mammalian host cell infected with a carrier virus, wherein said host cell comprises nucleic acid encoding proteins required for replication and encapsidation of the AAV stably integrated in its genome, wherein the carrier virus comprises a non-mammalian virus nucleic acid backbone that comprises a recombinant AAV genome comprising AAV ITRs and a transgene, nucleic acid encoding adenovirus helper function, and optionally comprises nucleic acid encoding a ligand expressed on the surface of the non-mammalian virus wherein the ligand binds a mammalian host cell, under conditions in which the recombinant AAV genome is replicated, excised and encapsidated.

9. The method of claim 8, wherein the mammalian host cell is selected from the group consisting of CHO, BHK, MDCK, 10T1/2, WEHI cells, COS, BSC 1, BSC 40, BMT 10, VERO, WI38, MRC5, A549, HT1080, 293, B-50, 3T3, NIH3T3, HepG2, Saos-2, Huh7 and HeLa cells.

10. The method of claim 8 wherein the mammalian host cell is a B-50 cell.

11. The method of claim 8 further comprising the step of collecting the recombinant AAV produced by the mammalian host cells.

12. The method of claim 8 wherein the non-mammalian virus is baculovirus.

13. The method of claim 8 wherein said adenovirus helper function is at least one function selected from the group consisting of adenovirus E1 function, E2a function, E4ORF6 function and VAI.

14. The method of claim 8 wherein said adenovirus helper function is E1 and E2a function.

15. The method according to either of claim 1 or 8 further comprising the step of purifying the recombinant virus from the mammalian host cells.

16. A method for producing a recombinant adeno-associated virus (AAV), comprising the step of growing a mammalian host cell transfected with a carrier vector, wherein said host cell comprises nucleic acid encoding proteins required for replication and encapsidation of the AAV stably integrated in its genome, wherein the carrier vector comprises a non-mammalian virus nucleic acid backbone that comprises a recombinant AAV genome comprising AAV ITRs and a transgene, nucleic acid encoding adenovirus helper function, and optionally comprises nucleic acid encoding a ligand expressed on the surface of the nonmammalian virus wherein the ligand binds a mammalian host cell under conditions in which the recombinant AAV genome is replicated, excised and encapsidated.

17. The method of claim 16, wherein the mammalian host cell is selected from the group consisting of CHO, BHK, MDCK, 10T1/2, WEHI cells, COS, BSC 1, BSC 40, BMT 10, VERO, WI38, MRC5, A549, HT1080, 293, B-50, 3T3, NIH3T3, HepG2, Saos-2, Huh7 and HeLa cells.

18. The method of claim 16 wherein the mammalian host cell is a B-50 cell.

19. The method of claim 16 wherein the non-mammalian virus is baculovirus.

20. The method of claim 16 wherein said adenovirus helper function is at least one function selected from the group consisting of adenovirus E1 function, E2a function, E4ORF6 function and VAI.

21. The method of claim 16 wherein said adenovirus helper function is E1 and E2a function.

* * * * *